US007700121B2

(12) United States Patent
Ben Achour et al.

(10) Patent No.: US 7,700,121 B2
(45) Date of Patent: Apr. 20, 2010

(54) GENE ASSOCIATED WITH LEISHMANIA PARASITE VIRULENCE

(75) Inventors: Yosser Ben Achour, La Marsa (TN); Mehdi Chenik, La Marsa (TN); Hechmi Louzir, La Marsa (TN); Koussay Dellagi, Tunis (TN)

(73) Assignees: Institut Pasteur, Paris (FR); Institut Pasteur de Tunis, Belvedere (TN)

( * ) Notice: Subject to any disclaimer, the term of this patent is extended or adjusted under 35 U.S.C. 154(b) by 379 days.

(21) Appl. No.: 10/733,232

(22) Filed: Dec. 12, 2003

(65) Prior Publication Data

US 2005/0119460 A1 Jun. 2, 2005

(51) Int. Cl.
```
A61K 39/00      (2006.01)
A61K 39/39      (2006.01)
A61K 39/002     (2006.01)
A61K 39/02      (2006.01)
A61K 45/00      (2006.01)
```
(52) U.S. Cl. .............. 424/269.1; 424/184.1; 424/185.1; 424/191.1; 424/234.1; 424/236.1; 424/278.1; 435/41; 435/69.1; 435/69.3; 435/70.1; 435/71.1; 435/243; 435/258.3; 435/320.1; 514/2

(58) Field of Classification Search .............. 424/151.1, 424/184.1, 185.1, 191.1, 192.1, 193.1, 265.1, 424/269.1, 278.1; 435/7.22, 9.2, 258.3, 342; 530/388.6; 930/210

See application file for complete search history.

(56) References Cited

FOREIGN PATENT DOCUMENTS

CA          2105538       4/1995

OTHER PUBLICATIONS

Blunt et al. 1996. Gene. vol. 181, pp. 221-223.*
Achour et al. 2002. Infect. & Immun. vol. 70(7): 3576-3585.*
Ivens et al. 1998. Genome Research. vol. 8(2): 135-145.*
Stiles et al. 1999. Ann Trop. Med. Parasitol. vol. 93(8): 781-807.*
Ravel et al. 1998. Parasitol. Today. vol.14(8):301-303.*
Padilla et al.; "Isolation of a Unique Protein-Disulfide Isomerase Gene from *Leishmania donovani*," Science Forum Poster Abstract, (2001).
Mandal et al.; "The Plasma-Membrane $Ca^{2+}$-ATPase of *Leishmania donovani* is an extrustion pump for $Ca^{2+}$;" Biochem. J. Vol. 322, No. 1, pp. 251-257, (1997).
Clive and Greene; "Association of Protein Disulfide Isomerase Activity and the Induction of Contact Inhibition;" Experimental Cell Research, vol. 214, No. 1, pp. 139-144, (1994).
Abdelhak et al.; "Recombinant BCG expressing the Leishmania Surface Antigen Gp63 Induces Protective Immunity Against *Leishmania major* infection in BALB/c mice;" Microbiology, vol. 141, pp. 1585-1592, (1995).
Lyles and Gilbert; "Catalysis of the Oxidative Folding of Ribonuclease A by Protein disulfide Isomerase: Dependence on the Rate of the Composition of the Redox Buffer;" Biochemistry, vol. 30, No. 3, pp. 613-619, (1991).
Mou et al.; "The Selective Inhibition of $\beta_1$ And $\beta_7$ Integrin-Mediated Lymphoctye Adhesion by Bacitracin;" The Journal of Immunology, vol. 161, No. 11, pp. 6323-6329, (1998).
Heard et al.; "*Leishmania mexicana amazonensis*: Differential Display Analysis and Cloning of mRNAs from Attenuated and Infective Forms;" J. Euk. Microbiol., vol. 43, No. 5, pp. 409-415, (1996).
Yu et al.; "Key Role for DsbA in Cell-to-Cell Spread of *Shigella flexneri*, Permitting Secretion of Ipa Proteins into Interepithelial Protrusions;" Infection and Immunity, vol. 68. No. 11, pp. 6449-6456, (2000).
Kébaier, et al.; "Heterogeneity of Wild *Leishmania major* Isolates in Experimental Murine Pathogenicity and Specific Immune Response;" Infection and Immunity, vol. 69, No. 8, pp. 4906-4915, (2001).
Murphy, et al.; "Leishmania major Friedline Assembled Shotgun Reads from Chromosome 36;" EMBL/GenBank/DDBJ database; Accession AL499624; Submitted May 18, 2001.
Norrish, et al.; "LmFrAm0479 Leishmania major Amastigote Full Length cDNA Library Leishmania major cDNA Clone Q52 5', mRNA Sequence;" Accession AA680895; Dec. 5, 1997.
Louzir; "Novel Gene Associated with Leishmania Parasite Virulence; Therapeutic and Vaccine Applications;" Pasteur Licensing Opportunity; url:www.pasteur.fr/applications/drl/English/Dl/00.80.html, 2000.
Rovai, et al.; "Recurrent Polymorphisms in Small Chromosomes of *Leishmania tarentolae* After Nutrient Stress or Subcloning;" Mol. Biochem. Parasitol., vol. 50, No. 1, pp. 115-125; (1992).

\* cited by examiner

*Primary Examiner*—Mark Navarro
*Assistant Examiner*—JaNa Hines
(74) *Attorney, Agent, or Firm*—Finnegan, Henderson, Farabow, Garrett & Dunner, L.L.P.

(57) ABSTRACT

The invention relates to the field of combating leishmaniases. Said invention results from the isolation, from wild isolates of *Leishmania major*, of a protein-coding gene known as LmPDI which has two regions that are identical to the sequence (Cys-Gly-His-Cys) of the potential active site of the protein disulphide isomerases (PDI). The LmPDI protein is predominantly expressed in the most virulent isolates of the parasite. Said protein forms a novel therapeutic target for developing anti-leishmaniasis medicaments and a novel element that can be used in the composition of immunogenic, and possibly vaccinating, preparations which are intended to protect a human or animal host against *Leishmania*.

3 Claims, 15 Drawing Sheets

Figure 2

Figure 3 A

Figure 1:
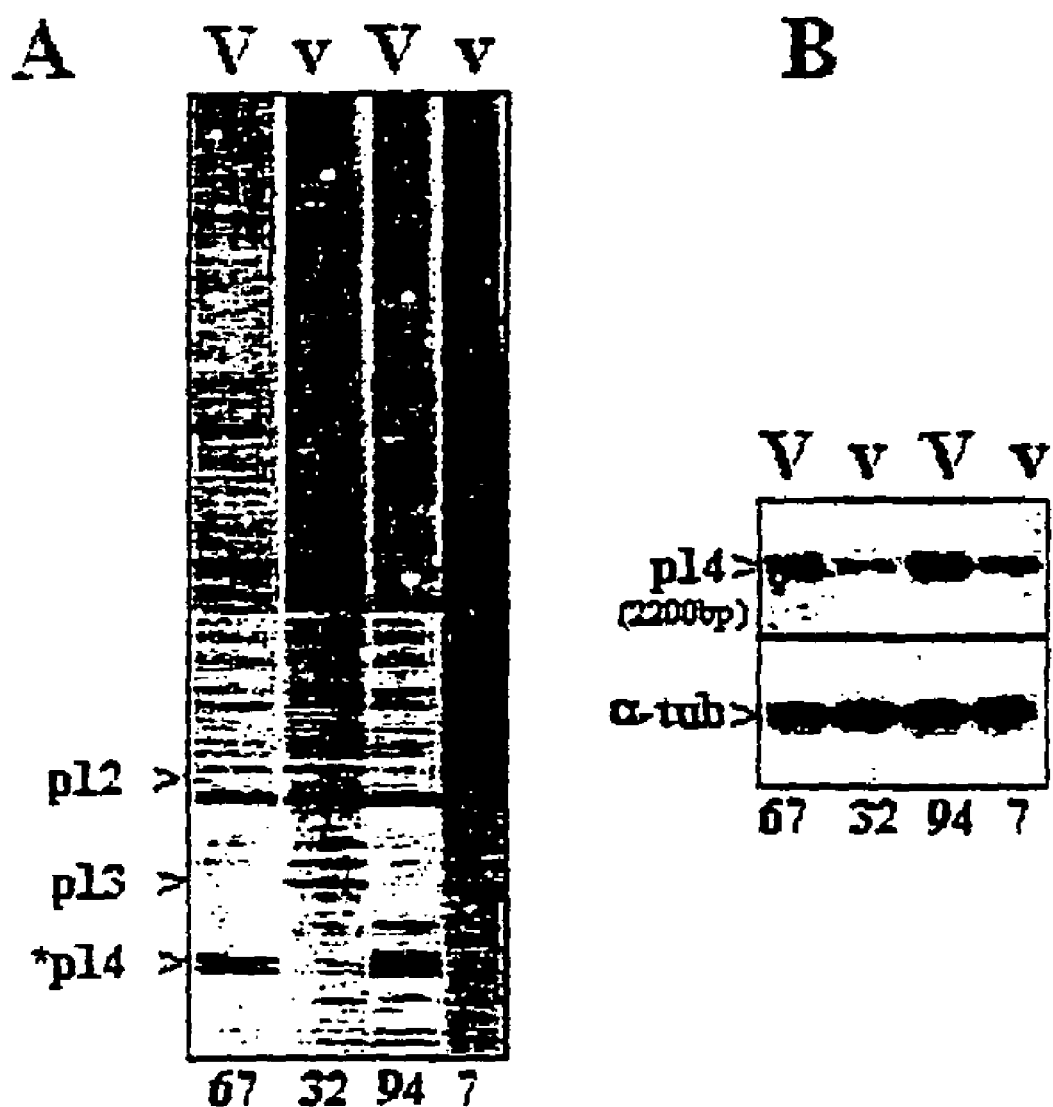

```
L. major      1  ----------------MQRS*IVFVI*CA*FCV*SA*VQ--------------*AIKDN**
T. brucei     1  ----------------MR*I*LV*LA*ATMRESTA*SLK--------------ITKEN-*N
H. jecorina   1  ----------------MQQKR*TAALVAA*AAVVSA*S*--------------MKS*TKDT*N
C. elegans    1  ------------MI**QAA*VASFLAF*SAGGA--------------*LEY*DGN**
C. reinhard   1  MNRWNLLA*TLGLL*VA*P*TKH*FAHASDEYED*DAPAAPKDDVDVIVVKN**
D. melano     1  ---------MKF*ICAL*L*A*SY*AASAEAEVKVE*--------------GVLVA*VDN*K
C. parvum     1  --------MIGIRS*VSAA*LGFSQ*SKVVLGS*AHFIS--------------EH*TS**SSNF*
H. sapiens    1  --------M*RRAL*CLAV*A*VRADP*--------------HV*LV*RKSN*A L. major     32  KV*IG-**TLV*F*YAPWCGHC*TLA*E*VKAADM*AGI*T----*A*VD**KSES*AEK**
T. brucei    31  *T*AKS**IFLV*KFYVDT*CGYC*M*APEEKAANETIDNLMG---*V*CHS*PE*AA***
H. jecorina  34  *F*NSN**L*A*S*APWCGHC*KA*APE*YEEA**T*KDKS--*R**AKVDCVE*A**CKEH*
C. elegans   32  *L*QTH**A*V*K*YAPWCGHC*KK*A*P*E*AKAATA*KAA*PDA**AKVDA*QBES**QKS*
C. reinhard  61  *T*KKSKFA*VEF*YAPWCGHC*KT*K*E*AKAA*PK*ASNDPP*A**V*EC*TEKT*CDK**
D. melano    39  QL*ADN*F**LVEF*YAPWCGHC*KALA*E*AKA**QQ*AEKESP*IK*AKVDA*VEGAEQ
C. parvum    45  *F*KSK*H*V*V*T**APWCGHC*TALE*P**KATCAE*SKLSPP**C*S*DA*ENMGAQG
H. sapiens   36  *A*AAHKY**LV*E*YAPWCGHC*KALA*PE*YAKA*GK*KA*C*S*IR*AKVLA*E*BS**AQ*YG L. major     88  *I**P*TI*YI*RNG*---KVKI*YD*PRT*A*G*ASM*KA*VG*SMKA*S*A*E**BB*KKETFP
T. brucei    88  *E*GYP*TI*IL*RNGK--EAEH*G*ARTK*DE*KN**ANV*PAVTPASNA**V*TRAKE*H*V
H. jecorina  92  V*G*YPTLKV*RGL*--KVA*E*G*PRK*DG*ITSE*V*QS-LP*VSAL*K*TE*DFKTADK*
C. elegans   92  V*K**PTLKI*RNG--VPA*Q*VDG*PRDADGI*VK*NEG*QS*G*SSKEVA*BF*KFTGGDEN
C. reinhard 121  V*QGYP*TL*KW*V*C--ELAS*DMNG*PRDADG*IVG*VK*ENTG*PA*VT*VED*A*K*KS*EADA*V
D. melano    99  V*K*GY*P*TL*KF*FR*SG---SPV*EY*SCG*RQA*ADL*A*V*T*G*GP*A*KD*PT*SVADAQFLK
C. parvum   105  VSGY*P*TK*K*FS*SGI*--SVQN*SCARSK*F*FIKY*E*K*L*G*PAVQVA*S*E*A*KT*FASSSS
H. sapiens   96  V*R*SYP*TLK*F*FRNGD*TASPK*E*Y*A*GRE*ADD*VN*T*LKE*RT*GP*A*TT*PD*CAAA*B*S*H*VESSE*V L. major    146  VC*VVKTASTT*SEM*SMIT*KV*ADS*RS*O*NFVLVTDAA*S*SPNDAMESVT-----*VYR*NA*
T. brucei   146  VC*V*LTANNS*S*LST**LAEA*QSFR*VS*KFFEAEPK*FPDEKPETIVVYR---------KG
H. jecorina 149  V**V*V*IAADD*KASNE*F*TA*C*ANE*RE*TYLFGGV*DAA*AEAEGVKFP---S-*DV*KS*D
C. elegans  150  *V*EESESKLKDSYLKVADTERDRFSU*SKD*T*KKAGYSDDVVVFVPKK*HNK**
C. reinhard 179  V**V*G**K*A*E*G*IYD*KSY*AKTE**V*E*VQ*TSA**VAKAAGLDAVDTSV-*KN*AGE*
D. melano   156  A**S*E*KD*ES**EAKE*TK*E*NA*LDSF**G*V*SSR*AD*LAKYEAR*DNG-----*LV*EKP**
C. parvum   163  AFVG*R*TSK*SAEYAV*ERA*SG*E*E*N*F*IAFF*OEGEQKLEVLHK----------*D
H. sapiens  156  AV*G*E*K*DV*ES*D*SAKQ*LQA*E*ALD**I*PE*EI*N*S*V*FSKYQLDKDG-----*VV*LEKKF*C L. major    201  REAYTGATP*TA*S*V*S**T*SAV*DYFC**LG*QB*S*FQK*YMEANKD*K*PLGWVF*D**N---TDS
T. brucei   198  GE*E*V*DE*P*E*V*EKE**TE*OI*SRV*AFG*E*V*TPEN*GYY*SVIKRP--VGWAM**KPNETASI
H. jecorina 205  *GKN*V*SEKF*A*BA**EN*AO*AAT*EV*GE*A*GP*E*I*AG*MSA**I*PLAY**FAETAE*---RE
C. elegans  210  TNEFK*D*GNY*D*TEK*I*KN**T*VHE*V*GFA*GIR*O*GL*FQ*E*OKPIVIVYYNVDY*W*DPKGSN
C. reinhard 238  RATA**LATD*DTP*S*T*AE*K*SEKY*SPTI*E*FNOK*SD*IFNS**INK*L*LWTTAD*LKADA
D. melano   211  *K*S*V*EG*E*NES*N*E*K*AOVQS*T*LIV*FR*SSAS*NIFG-*S*IR*SH*LFF*S*R**GGHIE
C. parvum   211  *EPVSLPMPKTVEE*EAK*S*IMNV*LFSA*SAB*NY*SLYMS--RE--GYTPGSVVLTRTSP
H. sapiens  211  *G*NN*E**G*V*TKENV*LLD*EI*KHNQL*E*VIE*F*E*QTAP*NIFG-*EIR*THILL*F*D*PKSVSDYD L. major    259  A*RGS*I*VAV*EK*Y*RSO*V*LTY*ID*G*LQ*R---PVSROLE*IP*E*AKFPAFV*D*FR**RI-*VMG
T. brucei   256  E*KES*L*T*DE*V*CK*M*S*E*K*VV*L*V*WH*ISKHF---*WRD*C*V*PE*AKYPAF*AIHWGAN-YLE*S
H. jecorina 262  N*AK*I**PV*DE*K*G*K*H**N*AL*DAKN*G--SHAGNIN*LN*T*D*KF*AF*A*HD**KNLKFPFD
C. elegans  270  YWRN*R*LK*V*QN*V*RE*V*QAVS*NK*E**SSEIE*NGL*GER*K**SDKP*IVA*LTNEG*A---YP
C. reinhard 298  E**V*TVF*REA*SK*G*Q*L**V*WNN*GDGADPV*ANF*GLK*GATS*V*DLGFF*KN*A--*FR*M
D. melano   270  KY*VDP*L*KE*L*AK*EY*RDD*L*L*V*LDS*SD*EEDHT*R*FEF*CV*NE*SEV*P*T*R*L*KE*BEDMA*KY*P
C. parvum   267  SM*QD*ER*L*OLITEKSY*PLFSI*DT*BOE*G-SHAI*OHL*L*EK*FPGLV*I*QS*LN*WPSI*-YMYG
H. sapiens  270  GK*LSNF*K*TA*E*S*L*KG*C**L*HE*FP*IDS*E*R*TDNOR*L*EF*GL*NKE*CPA*V*R*E*TL*EEMT*KY*P
```

Figure 3 B

```
L. major      316 TDTPVTSESVAAEVEKYVKGETKQTVMSDAEPAKETVNGEITVVGQTEAKYTDG-TQNVV
T. brucei     312 TAEVVIRESLEKETLEEAASRVEPITKSLEVPEVETVDGKTTEVAKTMQKHETS-GKDEL
H. jecorina   320 QSKETIEKDIAAFVDGESSGKEEASIKSEPIPETQ-EGPVTVVVAHSYKDIVLDDKKDVI
C. elegans    327 MDQEFSVINIQQEYDEVIAGNAEPYEKSEPIPDEQ--GDVKVAVGKNEKEILMDADKDVI
C. reinhard   357 EG-EFTADNVAKEAESVVDGTAQAVIKSEAIPEDPYEDGVYKEVGKTVESVVIDETKDVI
D. melano     330 ESDDISAETIEAETKKEFDGKEKQEILSDELPEDWDKNEVKVLVSSNEDSVALDKSKSVI
C. parvum     325 PAKFDSVEPLKEELMKQVSEGKHELSIKSEPIPAEQ-SGPVTVVVGKTFEEIVFRSDKDVI
H. sapiens    330 ESEEITAERITEECHREFLEGKEIKPELMSQELPEDWDKQPVKVLVGKNEEDVAFCEKKNVF L. major      375 ILEFYAPWCGHCKKEHPIYDKVAKSEES----ENVIIAKVDATINDFDREKEEVSGFPTIY
T. brucei     371 ILFEAPWCGHCKNFAPTEDKIAKEEDAT----DLIVAELDATANYVNSSTETVTAFFPTVF
H. jecorina   379 IEFYTPWCGHCKALAEKVDELASIYAKSDFKDKVVEAKVDATANDVP---DELQGFPTIK
C. elegans    385 IEFYAPWCGHCKSLADKYEELAEKLNK----BDVIIAKMDATANDVPPM-FEVRGFPTLF
C. reinhard   416 IEVYAPWCGHCKLEPIYKKLAKREKK---VDSVIIAKMDGEENEHPE--IEVKGFPTIL
D. melano     390 VEFYAPWCGHCKQLAPIYDQLAENYKD---NEDIVIAKMDSTANELES--IKUSSFPTIK
C. parvum     384 LEIYAQWCGHCKNLEDIYNOLGEEYKD---NDKVVIACINGPQNDIPYEGESPRAFPTIL
H. sapiens    390 VEFYAPWCGHCKQLAPIYDKLGETYKD---HENIVIAKMDSTANEVEA--VKVHSFPTIK L. major      431 FIPA--GKPPIVYEG-GRIADEIQVFVKSULT--------------ASAAPSGGPSGNS
T. brucei     427 EVPN--GGKPVVLEG-ERSFENVYEEVRKEVTTFKVSEKPANVTEEKKSEENKSSKSNE
H. jecorina   436 LYPAGDKNPVTESG-ARIVEDEIEELKENGKYKAGVEIPAEPTEEAEASESKASEEARA
C. elegans    440 WLEKNAKSNPIPLNG-GREVKEVSEISKES----------T---DGLKGFSREGKEK
C. reinhard   471 EYPAGSDETPIVEEGGDRSIKSLTKEINTNAKIPYELP---KRGSDGEEGTSDDKDKPAS
D. melano     445 YFRK-EDNKVIDNL-DRIIDDEVKEIDANE-----------EVADSEPVEETEEEEEAP
C. parvum     441 EVKA-GTRTEIPVEG-KRIVEAEKEEISEES-----------------SFPQE-KE
H. sapiens    445 FFPASADETVIDYNG-ERTIDGEKKEEESGGQDGAGDDDDLEDLEEAEEPDMEEDDQKA L. major      473 --------EEEDL
T. brucei     484 SNDSNESNVDKQEL
H. jecorina   495 SEET------EDEL
C. elegans    484 K---------KTEL
C. reinhard   528 D---------KDEL
D. melano     492 K---------KDEL
C. parvum     477 S---------EDEL
H. sapiens    504 V---------KDEL
```

GENE ASSOCIATED WITH LEISHMANIA PARASITE VIRULENCE

The invention relates to the field of the fight against leishmaniasis. It results from the identification, from wild isolates of *Leishmania major*, of a gene coding for a protein, designated LmPDI, having two regions identical to the sequence (Cys-Gly-His-Cys) of the potential active site of protein disulfide-isomerase (PDI). This LmPDI protein is predominantly expressed in the most virulent isolates of the parasite. It firstly constitutes a novel therapeutic target for developing anti-leishmaniasis drugs, and secondly, a novel element that can form part of the composition of immunogenic and possibly vaccinating preparations intended to protect a human or animal host against leishmaniasis.

Leishmaniases constitute a heterogeneic group of diseases that affect several million individuals and are due to infection of the host by a protozoic parasite of the genus *Leishmania*. Clinical expression of the infection is characterized by a high degree of polymorphism, including asymptomatic infection, simple or recurring cutaneous forms, diffuse or anergic cutaneous forms, mucocutaneous forms and visceral forms, which are fatal in the absence of specific treatment. In general, and depending on the geographical distribution of the disease, each species or sub-species of leishmaniasis is responsible for a particular clinical form; however, this is not a strict rule. Further, in the same geographical region, the same parasitic species can be responsible for clinical forms of varying severity. This diversity in clinical expression of the infection is at least partially due to a diversity in the virulence of the parasite.

During its cycle, the parasite alternates between two stages: the flagellate promoastigote stage, which is found in the digestive tract of the insect vector, and the amastigote stage in the host macrophage. Anti-leishmaniasis drugs are difficult to use, not least because they are toxic and because of the ever more frequent resistance developed by the parasite (Lira, Sundar et al, 1999). Further, recently developed and tested vaccines have so far not shown the expected efficacy (Sharifi, FeKri et al, 1998; Khalil, El Hassan et al, 2000).

The absence of tools for controlling leishmaniasis is partially explained by the complexity of the parasite transmission cycles and by the dearth of current knowledge regarding the biology of the parasite. During the last ten years, several molecules playing a fundamental role in the biology and infectivity of the parasite have been identified. Modifications to surface glyco-conjugates, particularly lipophospho-glycane (LPG), are associated with modifications to the infectivity and virulence of the parasite *Leishmania* (*L*) *major* and *L. donovani* (Beverley and Turco, 1998); Desjardins and Descoteaux, 1998; Sacks, Modi et al, 2000; Spath, Epstein et al, 2000), which does not appear to be the case for *L. mexicana* (IIg 2000; IIg, Demar et al, 2001). Molecules involved in the biosynthesis of LPG: phosphomannose isomerase (Garami and IIg, 2001), LPG1 (Sacks, Modi et al, 2000; Spath, Epstein et al, 2000), LPG2 (Descoteaux, Luo et al, 1995) and galactosyl transferase (De and Roy, 1999) have also been associated with the virulence of *Leishmania*. Other factors in virulence have recently been described. They include the family of cysteine proteases (Mottram, Brooks et al, 1998), mitogen activated protein (MAP)-kinases (Wiese, 1998), the A2 gene (Zhang and Matlashewski, 1997), the surface glycoprotein gp63 (Chakrabarty, Mukherjee et al, 1996), kinetoplastid membrane protein (KMP)-11 (Mukhopadhyay, Sen et al, 1998), superoxide dismutase (Paramchuk, Ismail et al, 1997), trypanothione reductase (Dumas, Ouellette et al, 1997), and certain members of the heat shock protein (HSP) family (Hubel, Krobitsch et al, 1997).

Characterizing virulence factors may have fundamental implications in the development of novel drugs or vaccines against these diseases. Preferential screening of a protein involved in the virulence of a parasite can avoid the unnecessary appearance of resistance in less dangerous strains, which resistances may then be transmitted to other strains. Further, a mutation of the targeted virulence protein causing resistance to the drug can in that case also cause a reduction or even loss of the virulence of the parasite and thus have a certain therapeutic effect.

Over the past decades, a number of approaches have been used to study the virulence factors for the *Leishmania* parasite. These approaches were based on genetic studies, such as the complementation of mutated parasites (Ryan, Garraway et al, 1993; Descoteaux, Luo et al, 1995; Desjardins and Descoteaux, 1997; Wiese, 1998), the use of the gene invalidation technique (Titus, Gueiros-Filho et al, 1995; Mottram, Souza et al, 1996; Dumas; Ouellette et al, 1997; Hubel, Krobitsch et al, 1997; Mottram, Brooks et al, 1998), or the analysis of genes for resistance to drugs on parasites manipulated in the laboratory (Cotrim, Garrity et al, 1999; Perez-Victoria, Perez-Victoria et al, 2001). Those studies identified several genes that were important to the biology of the parasite, and are currently being validated as targets for novel drugs (Selzer, Chen et al, 1997; McKerrow, Engel et al, 1999), or for the development and use of attenuated mutants as live vaccines (Titus, Gueiros-Filho et al, 1995; Streit, Recker et al, 2001). It is important to point out almost all of the studies carried out up to now on the virulence of the parasite *Leishmania* are based either on laboratory clones which have lost their virulence after prolonged culture, or on parasites genetically manipulated by mutagenesis experiments, gene invalidation or gene overexpression. Thus, it is possible that the conclusions relating to the virulence of the genes identified under these conditions are not actually relevant to the natural pathogenicity of the parasite in the transmission regions.

With the aim of studying the molecular bases for the virulence of the parasite, avoiding the methodological bias linked to the use of laboratory strains, the inventors initially isolated wild strains of *Leishmania* (*L*) *major* with different levels of virulence. *L. major* is the agent in zoonotic cutaneous leishmaniasis (ZCL), which exists in epidemic proportions in man over a very wide area which extends seamlessly from Mauritania to Mongolia. The inventors identified isolates of *L. major* obtained from human ZCL lesions, all obtained during the same transmission season, and which differ in their pathogenicity in an experimental model of the infection in BALB/c sensitive mice (Example 1). The differences in experimental pathogenic power correlate with the differences in growth in vitro, which reflects the variations in the biology of these wild isolates.

The "differential display" technique (Liang and Pardee, 1992; Liang, Bauer et al, 1995) was then used to identify genes differentially expressed between completely different isolates through their experimental pathogenic power in the BALB/c mouse (two highly virulent isolates and two other less virulent isolates). This technique allows genes which are expressed at different levels to be studied without knowing their sequence in advance. Three transcripts that are preferentially expressed in the two most virulent isolates were then identified. One of these transcripts was completely characterized by dint of screening a cDNA library of *L. major*. An analysis of the sequence demonstrated a homology with the protein disulfide-isomerase family (PDI, Erp60 and Erp72) in eukaryotes. This novel protein has been designated LmPDI for the following reasons: like other members of the PDI family, (i) LmPDI possesses two CGHC active regions, (ii) the N-terminal region of this protein contains in a potential signal sequence and, in the carboxy-terminal region, a potential signal for retention in the endoplasmic reticulum (EEDL); (iii) it can organize itself into an oligomeric structure; (iv) the recombinant protein produced in E. coli expresses PDI activity in vitro. Further, outside the conserved regions mentioned above, there are very few similiarities between LmPDI and the other PDIs described above. In fact, the PDI family includes a plurality of highly divergent molecules involved in the maturation of proteins secreted into the endoplasmic reticulum (Noiva 1999; Frand, Cuozzo et al 2000). PDIs are multi-functional proteins which are involved in complex mechanisms of retention, repair, regulation of expression; they assist changes in conformation to allow only correctly folded proteins to leave the endoplasmic reticulum. In addition to their enzymatic functions (reduction and isomerisation), other functions have recently been attributed to PDIs; they include chaperone activities, the binding of peptides and cellular adhesion (Ferrari and Soling, 1999). It is important to emphasize that LmPDI is predominantly expressed in the most virulent isolates (Example 2). In total, these results suggest that LmPDI plays an important role in the natural virulence of the *Leishmania* parasite, and can thus constitute a novel target for chemotherapy or vaccination.

Further, recent data regarding the involvement of the bacterial equivalent of PDIs (Martin, 1995; Ostermeier, De Sutter et al, 1996) (termed DsbA, disulphide bond) make suggestions regarding the role this protein could play in the pathogenicity of different micro-organisms (Yu and Kroll, 1999). Deactivation of the DsbA gene dramatically affects the survival and virulence of *Shigella flexneri* (Yu, 1998; Yu, Edwards-Jones et al, 2000). DsbA is also involved in the genesis of the enterotoxin of *Vibrio cholerae* (Peek and Taylor, 1992; Yu, Webb et al, 1992). DsbA also important for the pathogenicity of pathogenic *Escherichia coli* species: in species that are pathogenic for the urinary tract, it catalyses the formation of disulfide bridges of a specific chaperone protein of pilin (Zhang and Donnenberg, 1996). In enteropathogenic species, it is also required for the stability and formation of pili (Hultgren, Abraham et al, 1993; Wang, Bjes et al, 2000).

The present application constitutes the first description suggesting an important role for PDIs as a virulence factor in a protozoic parasite. LmPDI could exert its effects by assisting changes in the conformation and stability of other factors essentially to the biology and pathogenicity of the parasite *Leishmania*. Identifying such factors would be extremely advantageous for a better comprehension of the biology of this parasite, and for the development of novel treatments or vaccines against leishmaniases.

Thus, in a first aspect the invention concerns a protein involved in the virulence of *Leishmania*, comprising at least one (Cys-Gly-His-Cys) site identical to the potential active site of a protein from the protein disulfide-isomerase family (PDI). This protein is preferably a protein coded by the parasite itself.

In particular, the invention concerns the LmPDI protein of *Leishmania major*, with sequence SEQ ID No: 2, and any functional variant of LmPDI having at least 40% identity, preferably at least 80% identity with LmPDI.

We shall define here a "functional variant of LmPDI" as a protein that is capable of complementing LmPDI in an infectivity test carried out with a strain of *L. major* in which the LmPDI gene has been deactivated. The term "infectivity test" as used here means any test that can evaluate the biological properties relating to the growth of the parasite conventionally associated with virulence. In particular, the three following types of tests can be cited:

- growth kinetics in a liquid medium of the promastigote form of the parasite, for example by a technique of the type described in point 2 of Example 5;
- the infection capacity of mouse macrophages cultivated in vitro, using a technique such as that described in Example 6 and in the article by Kebaïer et al, 2001;
- the capacity to induce experimental murine leishmaniasis by infecting sensitive mice (BALB/c, for example). The technique is detailed in point 3 of Example 5, for example, and in the article by Kebaïer et al, 2001.

The percentage of identity with LmPDI are evaluated using CLUSTAL W version 1.8 software (Thompson J D, Higgins D G and Gibson T J) or BOXSHADE version 3.21 software (Hoffman K and Baron M) which produced percentage identities of LmPDI with proteins from the PDI family of several species as between 27% and 36% (Example 2).

In a second aspect, the invention concerns a recombinant polypeptide comprising at least one fragment of more than 10 amino acids of a protein as defined above, if appropriate fused with a further polypeptide fragment, said recombinant polypeptide being capable of triggering an immunological reaction against an epitope of LmPDI when administered to an animal. The invention also concerns a recombinant polypeptide comprising at least one fragment of more than 10 amino acids of a protein as defined above, if appropriate fused with a further polypeptide fragment, said recombinant polypeptide being capable of being recognized by antibodies directed against the LmPDI protein.

Throughout this text, the term "polypeptide" should be taken in its broad sense, i.e., including sequences of at least 10 amino acids (or more when stated), which may or may not comprise glycosylated motifs or glycolipids, and regardless of its primary, secondary or tertiary structure. The LmPDI fragment present in the recombinant polypeptides of the invention described above may be over 15, 20, 30, 50 or 100 amino acids in size, or even more.

The LmPDI, recombinant or purified from infected cells, and a polypeptide of the invention can be used to immunize a human or animal host, to protect it from leishmaniasis or to produce and recover antibodies directed against LmPDI, as described in Example 2.

A particular recombinant polypeptide of the invention is the LmPDI-$(His)_6$ protein with sequence SEQ ID No: 3, described in Example 2.

A further example of the recombinant polypeptide of the invention is a fusion protein between a LmPDI fragment comprising at least one epitope of LmPDI and a carrier polypeptide contributing to the presentation of that fragment to the immune system. It can in particular be a fusion of all or a portion of the LmPDI with a fragment of β-lactamase, or a tetanus or diphtheria anatoxin, or any other polypeptide from a pathogenic organism, in particular of parasitic, bacterial or viral origin.

In a further aspect, the invention concerns a nucleic acid sequence coding for a protein or a polypeptide as described above. A preferred nucleic acid sequence comprises the sequence coding for LmPDI with sequence SEQ ID No: 1, or a fragment of said sequence with a size of 30 nucleotides or more, preferably more than 100 nucleotides, coding for a polypeptide comprising at least one characteristic epitope of LmPDI.

The invention also concerns a nucleic acid vector comprising a nucleic acid sequence of the invention. As an example, it may be a plasmid, a cosmid, a phage or a virus. Preferably, a vector of the invention will allow expression in a host cell of a protein or a polypeptide in accordance with the invention. In particular, a vector of the invention can allow expression of LmPDI in a bacterial or eukaryotic cell.

The invention also pertains to a cultured cell comprising a vector as defined above. Said cell can be a bacterium, a yeast, an insect cell, a mammalian cell or any other type of cell. It can be used either to express and possibly produce a protein or a polypeptide in accordance with the invention, or to produce a vector which will then serve to express a protein or a polypeptide in accordance with the invention in a further cultured cell type, or in vivo. Purely by way of non-limiting illustration, CHO, VERO, BHK21 cells and insect cells can be cited as cell types that can be used in vitro in the context of the present invention. Similarly, BCG and *Salmonella typhimurium* can be cited as cells that can be used in vivo. Finally, it is important to note that administration to an individual of a viral vector, for example a vaccine virus or DNA coding for a polypeptide or a protein as described above for vaccine purposes is also encompassed within the scope of the invention.

A particular cell of the invention is the bacterial strain LmPDI-XL$_1$ deposited at the Collection National de Culture des Microorganismes [CNCM, the National Collection of Microorganism Cultures], on 31 Jan. 2002 with accession number I-2621. This strain is derived from a XL1-blue MRF' strain bacterium with genotype Δ(mrcA)183 Δ(mcrCB-hs-dSMR-mrr)173endA1 sup E44 thi-1 recA1gyrA96 relA1 lac [F' proAB lac $^q$Z ΔM15 Tn10 (Tet')], transformed by the plasmid pBK-CMV-LmPDI. This plasmid corresponds to the plasmid pBK-CMV sold by Stratagene (La Jolla, Calif.) to which cDNA from LmPDI has been added between the EcoRI and Xho I restriction sites.

The invention also pertains to a nucleic acid probe, which specifically hybridizes under stringent conditions with the nucleic acid sequence of SEQ ID No: 1, allowing the presence or absence of the virulence gene coding for LmPDI to be determined in a biological sample.

"Stringent hybridization conditions" are defined herein as conditions that allow specific hybridization of two DNA molecules at about 65° C., for example in a solution of 6×SSC, 0.5% SDS, 5×Denhardt's solution and 100 μg/ml of denatured non specific DNA or any solution with an equivalent ionic strength, and after a washing step carried out at 65° C., for example in a solution of at most 0.2×SSC and 0.1% SDS or any solution with an equivalent ionic strength. However, the stringency of the conditions can be adapted by the skilled person as a function of the size of the sequence to be hybridized, its GC nucleotide content, and any other parameter, for example following protocols described by Sambrook et al, 2001 (Molecular Cloning: A Laboratory Manual, 3$^{rd}$ Edition, Laboratory Press, Cold Spring Harbor, N.Y.).

In the above definition, and throughout the present text, the term "specific" should be taken to have its broadest meaning, normally used in laboratories. Thus, a molecule A specifically recognizes a molecule B if, in a complex mixture, molecule A has an affinity for molecule B that is significantly higher than its affinity for other molecules of the mixture, so that it is possible to detect molecule B via molecule A.

The stringency conditions used here are those that allow the PDIs of different *Leishmania* species to be detected rather than those of the host and other microorganisms in the presence of a radiolabelled probe synthesized from the cDNA of LmPDI.

As an example, a probe of the invention, which specifically hybridizes with sequence SEQ ID No: 1 under stringent conditions, is such that a Southern blot carried out using said labeled probe, when carried out on a DNA sample from cells infected with a strain of *L. major* expressing LmPDI, has at least one clearly distinct band of higher intensity than other bands (non specific), said band not appearing on a Southern blot carried out under the same conditions on a DNA sample from cells not infected by a strain of *L. major*.

In a further aspect, the invention concerns a nucleotide primer that can allow specific amplification of at least a portion of the sequence SEQ ID No: 1, from cells infected with *Leishmania*, thus allowing the presence or absence of the virulence gene coding the LmPDI to be determined in a biological sample. Amplification will be termed "specific" if the amplification reaction carried out from control cells not infected with *Leishmania* does not result in significant amplification of any sequence, while the same reaction carried out on a sample containing the nucleotide sequence of SEQ ID No: 1 results in amplification of at least one fragment of said sequence.

The probes and primers mentioned above can if necessary be labeled and/or presented in diagnostic kits which also form part of the invention. It may be advantageous to determine the presence and possibly the level of expression of the gene for LmPDI during an infection with *Leishmania*, for example to determine the parasitic and/or opportunistic charge of a treatment involving the use of a LmPDI inhibitor.

In a further implementation, the invention provides purified antibodies specifically recognizing LmPDI. They may be monoclonal or polyclonal human, humanized or animal antibodies. Said antibodies can be purified, for example, on an LmPDI affinity column using the protocol described in the experimental section. Said specific LmPDI antibodies may have a number of applications.

They may serve to detect the presence of LmPDI in a biological sample, for example to diagnose leishmaniasis and/or to determine the possibility of using a LmPDI inhibitor to treat that leishmaniasis.

Thus, the invention also concerns an in vitro method for diagnosing an infection by a parasite responsible for leishmaniasis. Such a method can be carried out using a polypeptide or a protein of the invention or an antibody directed against that protein, or using probes as defined above.

A particular diagnostic method of the invention comprises the following steps:
  bringing at least one antibody in accordance with the invention into contact with a biological sample from a subject partially infected by a parasite responsible for leishmaniasis under conditions allowing the formation of an immune complex between said antibody and antigenic proteins contained in the sample;
  detecting said complex.

The complex can be detected using any means that is known to the skilled person (enzymatic reaction, fluorescence transfer or the like).

The antibodies of the invention can be comprised in diagnostic kits in the same manner as the probes or primers mentioned above.

Diagnostic kits for implementing the method described above form an integral part of the present invention.

By way of example, such a kit can comprise
  at least one antibody in accordance with the invention;
  a medium suitable for forming an immune complex between the antigenic proteins contained in the analyzed sample and said antibody;
  reagents allowing the detection of the complexes so formed;
  if appropriate, control samples.

Alternatively, the antibodies of the invention can form part of the composition of a drug intended for prophylaxis, attenuation or for the treatment of certain leishmaniases.

In a further aspect of the invention, the invention pertains to an immunogenic composition comprising a protein and/or a recombinant polypeptide and/or a nucleic acid sequence and/or a vector and/or a cell of the invention as described above, said immunogenic composition being capable of in vitro stimulation of the proliferation of mononuclear cells deriving from individuals who have come into contact with a *Leishmania* parasite. A preferred immunogenic composition of the invention is capable of in vitro stimulation of the proliferation of mononuclear cells deriving from individuals who have come into contact with *Leishmania major*.

In a preferred implementation of the immunogenic compositions of the invention, said compositions have a formulation that is pharmaceutically acceptable for administration to a human or animal host.

The inventors have shown that LmPDI is susceptible of in vitro induction of the production of cytokines by mononuclear cells deriving from individuals who have come into contact with *L. major*, and that the expression profile of the cytokines corresponds to that observed during a type Th1 immune response (Example 3). An immunogenic composition as described above, which is capable of inducing a type Th1 immune response when administered to a human or animal host, thus constitutes a particularly preferred implementation of the present invention.

The invention also pertains to a vaccine composition comprising a protein and/or a recombinant polypeptide and/or a nucleic acid sequence and/or a vector and/or a cell of the invention as described above, said vaccine composition being intended to protect a human or animal host against leishmaniasis. Preferably, the vaccine compositions of the invention are formulated in a manner that is pharmaceutically acceptable for administration to a human or animal host.

Said vaccine composition can be in the liquid form for injection into a patient, either subcutaneously or intramuscularly, or in the form of an oral vaccine, in the form of a pomade, or in the form of particles bound to a nucleotide sequence of the invention, for example by DNA adsorption onto the particle surface. This latter form allows the vaccine to be administered using a gene gun. It is important to note that the formulations for the vaccine compositions mentioned here are given solely by way of example and are in no way restrictive.

The immunogenic and/or vaccine compositions of the invention can also comprise one or more antigen(s) that are heterologous as regards *Leishmania*, and/or one or more nucleic acid sequence(s) coding for said antigens. The compositions of the invention can thus trigger an immunological reaction against several different pathogens and if appropriate may constitute polyvaccines.

The vaccination process and the doses of active agent must be adapted to the type of vaccine used and to the mammal to which it is administered.

Methods for vaccination against *Leishmania*, consisting of administering a composition comprising a protein and/or a recombinant polypeptide and/or a nucleic acid sequence and/or a vector and/or a cell of the invention as described above to a human or animal host, are also encompassed by the invention.

Determining the role of LmPDI in the virulence of *Leishmania* can also enable novel strategies for identifying active molecules for inhibiting the growth of the parasite to be envisaged. It has been shown that a molecule inhibiting PDI, for example, such as bacitracin or chloromercuribenzene sulfonic acid (pCMBS), inhibits the growth of *Leishmania* in a liquid medium (Example 4). Thus, the invention also pertains to a method for screening molecules susceptible of inhibiting the growth of *Leishmania major*, comprising a step for evaluating the capacity of said molecules to inhibit the activity of LmPDI. Protein disulfide-isomerases in general have a plurality of activities, in particular oxido-reduction, isomerase, and chaperone activities. The screening methods of the invention can pertain to the inhibition of any of the functions of LmPDI.

In a particular screening method of the invention, the step for evaluating the capacity of a molecule to inhibit the activity of LmPDI is carried out in a test for reactivating scrambled RNase A, comprising the following steps:

- incubating scrambled RNase A in the presence of LmPDI under conditions allowing its reactivation;
- incubating scrambled RNase A under conditions identical to those allowing its reactivation by LmPDI, the molecule to be tested being added;
- comparing the results obtained in the absence and in the presence of the test molecule, a fault in the reactivation of RNase A in the presence of the test molecule revealing that said molecule has an LmPDI inhibiting activity.

Any other PDI activity test can be used in the screening methods of the invention, in particular any test derived from the initial protocol described by Lyles and Gilbert (1991).

A screening method of the invention can also comprise a test for inhibiting the growth of *Leishmania major* in a liquid medium and if appropriate, a test for inhibiting the growth of *Leishmania major* in an experimental murine model of leishmaniasis. An example of such a method is described in the experimental section, Example 5.

The active molecules screened by the method defined above are characterized by their capacity to inhibit or modulate the growth of *Leishmania major.*

The results obtained with bacitracin shown in Example 4 show that a PDI inhibitor can inhibit the growth of *Leishmania* The use of one or more protein disulfide-isomerase (PDI) inhibitors for the preparation of a pharmaceutical composition intended for prophylaxis, attenuation, or treatment of an infection with *Leishmania* thus forms an integral part of the invention. Compounds with an anti-PDI activity that can be used in accordance with the invention that can be cited are anti-PDI or anti-LmPDI antibodies, bacitracin, zinc bacitracin, 5,5'-dithiobis(2-nitrobenzoic) acid (DTNB), p-chloromercuribenzene sulfonic acid (PCMBS) or tocinoic acid.

The compositions prepared in accordance with the above uses can preferably be topically, orally or parenterally administered to a human or animal host.

In accordance with a particular aspect, the invention concerns the use of bacitracin or zinc bacitracin as an inhibitor to the growth of a parasite responsible for leishmaniasis or as an active agent against a *Leishmania* infection.

Clearly, a pharmaceutical composition for the treatment of an infection with *Leishmania* containing one or more protein disulfide-isomerase (PDI) inhibitors forms an integral part of the invention. Such a composition can in particular contain bacitracin or zinc bacitracin. The composition can be formulated for topical application, for example in the form of a cream, an ointment, a pomade, or a spray, this list being non-limiting. The inventors have shown that such a composition, applied locally in the form of a pomade to the injection site of the parasite in BALB/c mice, attenuates the progress of the disease (Example 9 and FIG. 14).

The present invention also pertains to a pharmaceutical composition for the treatment of an infection with *Leishmania*, comprising at least one specific antibody for LmPDI and/or any molecule that inhibits PDI activity. Such a composition is preferably appropriate for topical, oral or parenteral administration.

Methods for treating leishmaniases, comprising administration of a PDI or LmPDI inhibitor to a human or animal patient, whether an antibody or any other type of molecule, also fall within the scope of the invention.

The examples and figures below describe the biological experiments which have been carried out in the context of the present invention and which provide the required experimental support, without in any way limiting its scope. They also illustrate, in a non restrictive manner, certain aspects of the implementation and importance of the present invention.

KEY TO FIGURES

FIG. 1 shows a differential display (DD) analysis of the expression of Leishmania major genes in the two most virulent isolates (94 and 67, V) and the two least virulent isolates (32 and 07, v).

FIG. 1A shows a portion of a sequencing gel after autoradiography, showing the products amplified by PCR using an arbitrary decamer and an oligo dT primer. The differentially expressed cDNAs are indicated by arrows. The p14 cDNA is indicated by an asterisk.

FIG. 1B shows a Northern blot analysis of the expression of a gene identified by the DD technique between the most virulent isolates (94 and 67, V) and the least virulent isolates (32 and 07, v). The mRNA extracted from the promastigotes from different isolates in the stationary growth phase were hybridized with the radiolabelled probe p14. After autoradiography, the blots were de-hybridized then re-hybridized with a specific probe for the gene for the α-tubuline of L. Major (α-tub).

Figure 2:
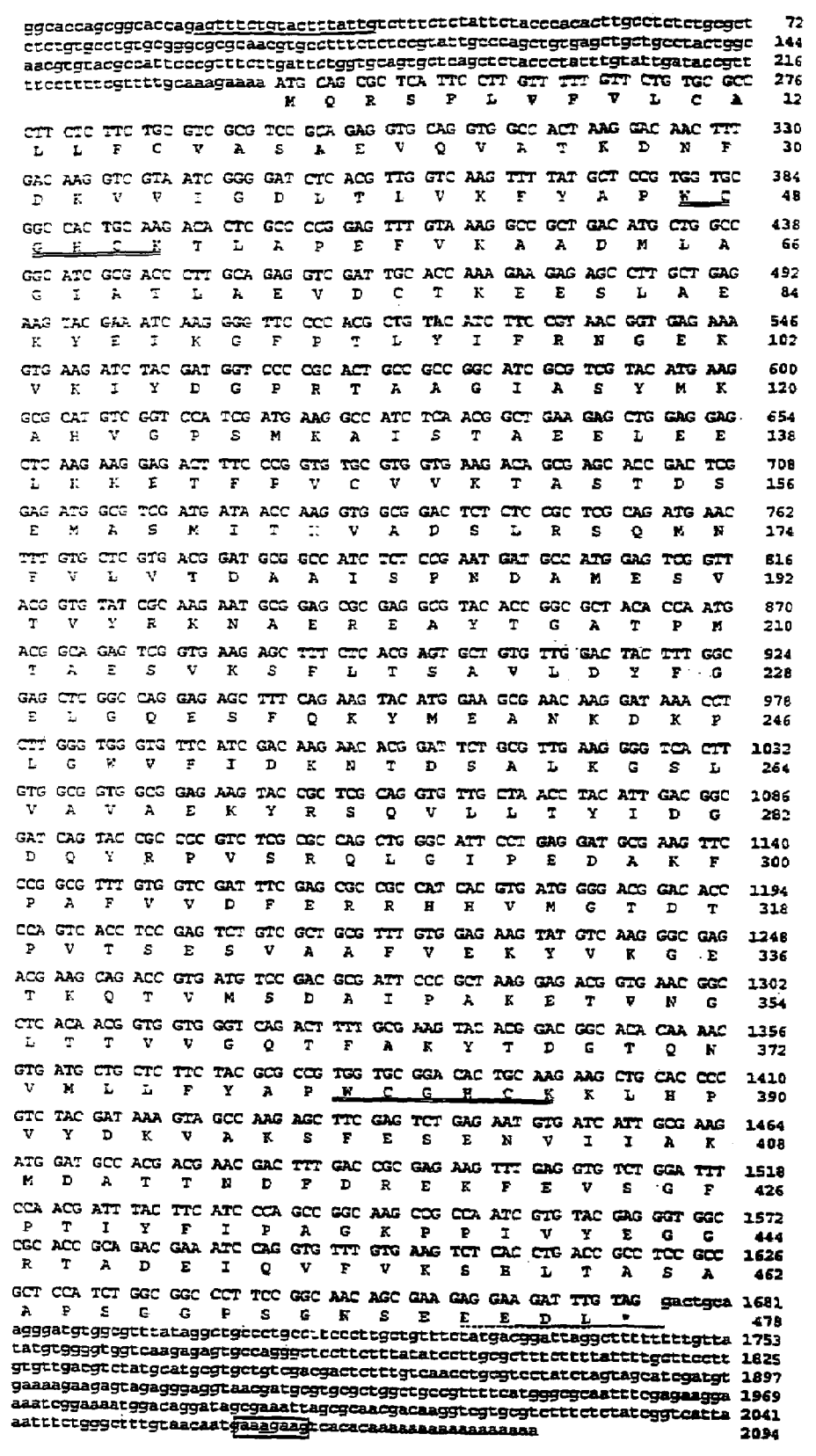

FIG. 2 shows the nucleotide sequence for the cDNA (SEQ ID No: 1) of LmPDI and the deduced sequence of amino acids (SEQ ID No: 2). The nucleotides in lower case letters represent non-translated regions. The leader sequence (SL) of 18 nt is underlined and the potential sequence for the polyadenylation signal is boxed. The potential sequence for the peptide signal is shown in bold. The potential active sites for LmPDI are double underlined and the probable sequence for retention in the endoplasmic reticulum is shown as a broken line.

FIG. 3 shows the alignment of the amino acid sequence for LmPDI with the protein disulfide-isomerase of Trypanosoma brucei (T. brucei, GenBank accession no.: P12865, SEQ ID No: 4), Hypocrea jecorina (H. Jecorina, 074568, SEQ ID No: 5), Caemorhabditis elegans (C. elegans, 017908, SEQ ID No: 6), Chlamydomonas reinhardtii (C. reinhard, 048949, SEQ ID No: 7), Drosophila melanogaster (D. melano, P54399, SEQ ID No: 8), Cryptosporidium parvum (C. parvum, Q27553, SEQ ID No: 9), and Homo sapiens (H. sapiens, P072237, SEQ ID No: 10). The letters boxed in black indicate identical amino acids and those boxed in gray indicate similar amino acids. The "gaps" were introduced to obtain the maximum similarity between the aligned sequences and are indicated by dashes.

Two software programs were used to carry out the alignments:
CLUSTAL W version 1.8; Thompson, J D, Higgins, D G and Gibson, T J;
BOXSHADE version 3.21; Hoffman, K and Baron, M.

Figure 4:
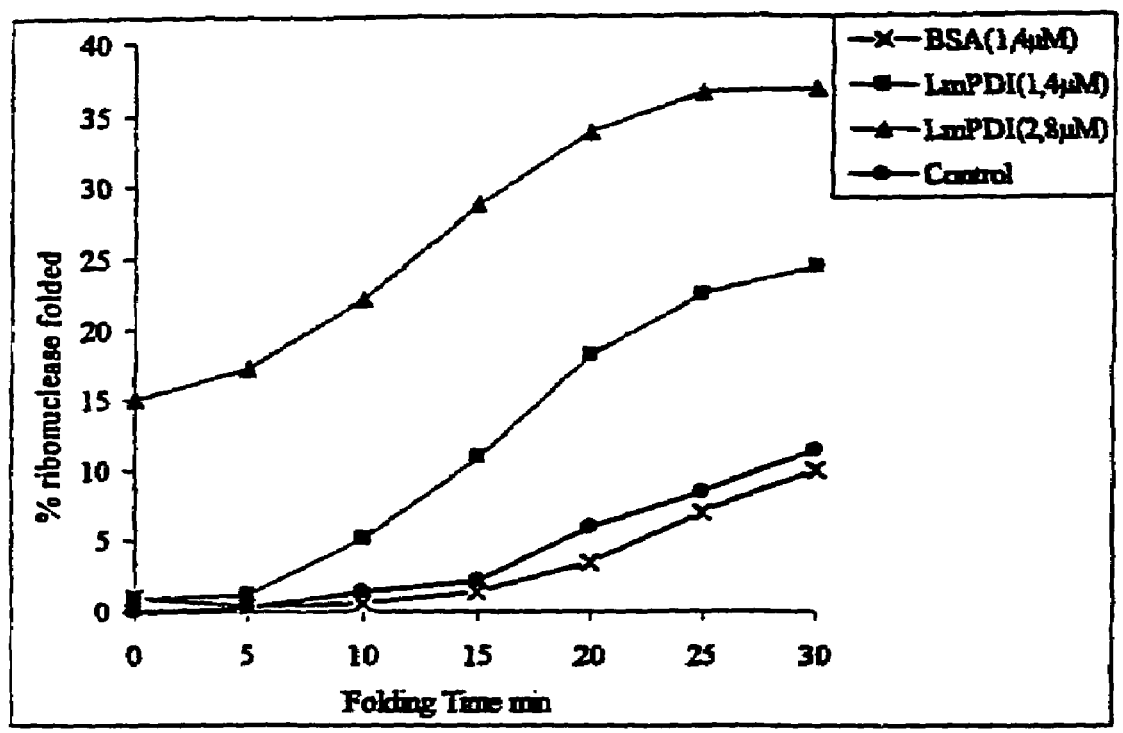

FIG. 4 shows an analysis of the role of recombinant LmPDI in reactivating scrambled RNase. Scrambled RNase A (8 μM) was incubated in a buffer containing 4.5 mM (cCMP), 1 mM glutathione GSH, 0.2 mM glutathione disulfide GSSH, 2 mM EDTA and 100 mM Tris-HCl pH 8 in the presence of bovine serum albumin (BSA) (1.4 μM) as a negative control, bovine protein disulfide-isomerase (1.4 μM) as the positive control, or recombinant LmPDI (1.4 μM) for 30 minutes at 25° C. RNase A reactivation was determined by measuring the RNase A activity at 296 nm every 5 minutes for 30 minutes (Lyles and Gilbert, 1991).

FIG. 5A shows a Southern Blot analysis for the number of copies of the LmPDI gene in the Leishmania major gene. 8 μg of isolate genomic 94 DNA from L. major was digested by the following restriction enzymes: AvaI, EcoRV, HindIII, PstI, EcoRI, XhoI, NcoI, SacI, SphI. The enzymes marked with an asterisk cleave once within the cDNA of LmPDI.

FIG. 5B shows a Southern Blot analysis of the LmPDI gene in different species of Leishmania. 8 μg of genomic L. major DNA (94), dermotropic L. infantum (L. infantum MC), viscerotropic L. infantum (L. infantum Visc); L. donovani were digested with the PstI enzyme. Genomic DNA was hybridized in these experiments by the probe representing the entire cDNA sequence of LmPDI.

Figure 6:
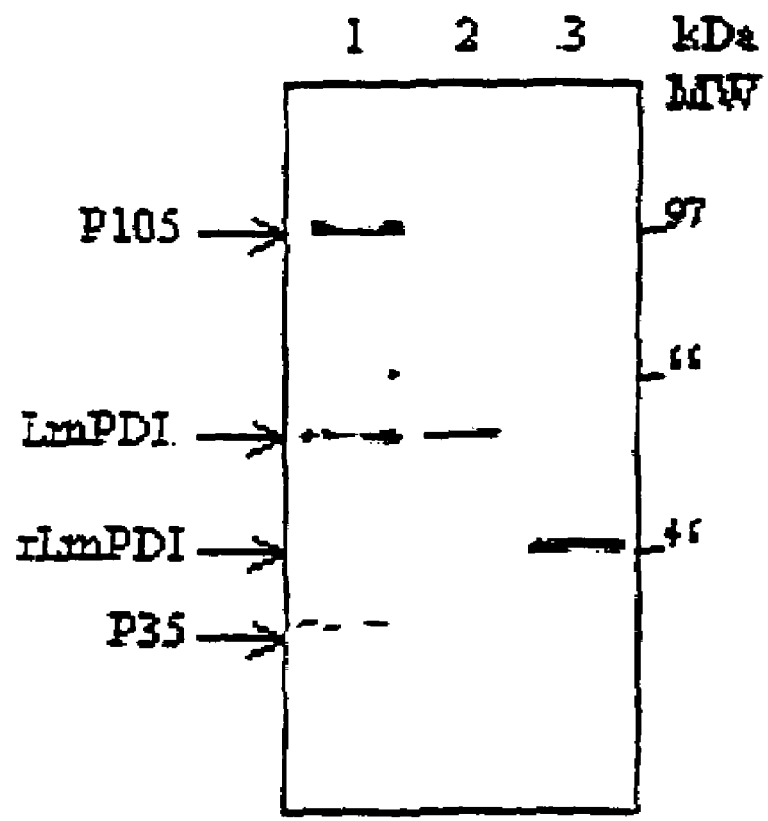

FIG. 6 shows immunodetection of native LmPDI in L. major with different preparations of anti-LmPDI antibodies. 20 μg of total promastigote GLC 94 proteins in Laemmli buffer (track 1) or in the presence of 0.5 m of DTT (track 2) and 0.05 μg of LmPDI produced in E. coli bacteria and purified (rLmPDI) (track 3) underwent electrophoresis then were transferred onto a nitrocellulose membrane, then revealed with an anti-LmPDI immunoserum (track 1) or anti-LmPDI antibodies purified on an affinity column (tracks 2 and 3).

Figure 7:
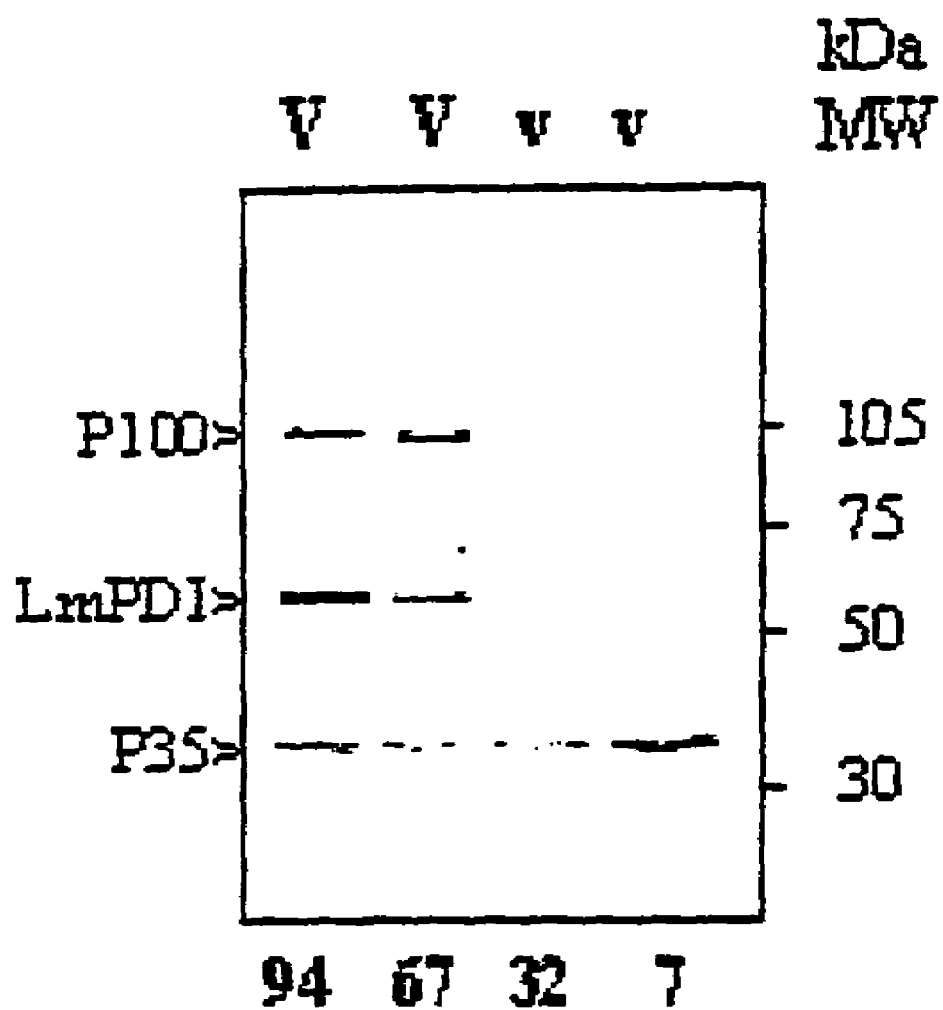

FIG. 7 shows a Western blot analysis of the expression of LmPDI in the two most virulent isolates (94, 67, V) and the two least virulent isolates. (32, 7, v) from promastigotes. 20 μg of total promastigote protein in the stationary growth phase from different isolates underwent electrophoresis and were then transferred onto a nitrocellulose membrane which was incubated in the presence of polyclonal anti-LmPDI antibody. The arrows (>) indicate the 3 proteins recognized by the anti-LmPDI immunoserum.

Figure 8:
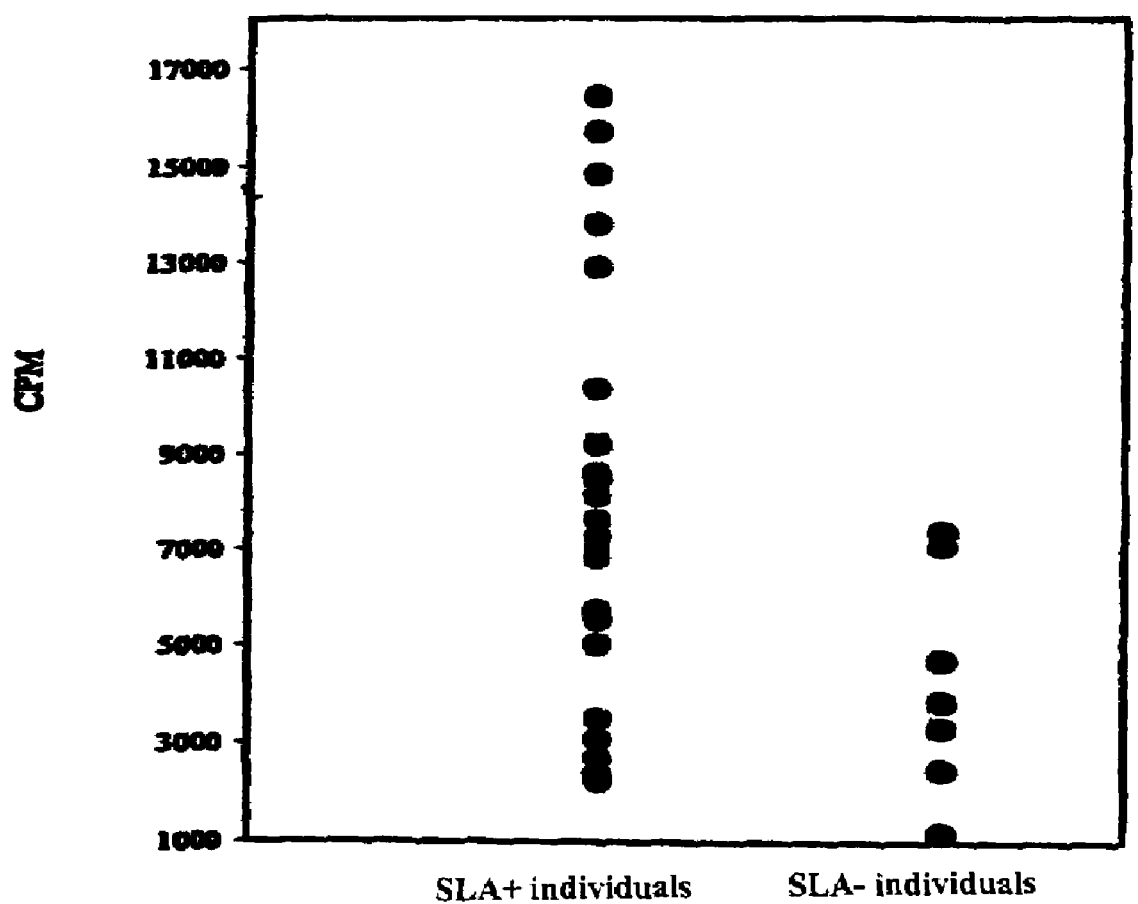

FIG. 8 shows the proliferation of mononuclear cells from individuals living in a zoonotic cutaneous leishmaniasis region in Tunisia, after incubation of LmPDI (5 μg/ml). The lymphomonocytary cells were recovered, washed by 3 successive centrifuge runs with RPMI-PS/Glu medium (30 ml then twice 10 ml) then counted and incubated at a concentration of $10^6$ cells/ml of medium in the presence or absence of a concentration of 5 μg/ml of LmPDI. After 5 days of culture, lymphocyte stimulation was estimated by incorporating tritiated thymidine. The result is expressed in CPM.

Figure 9:
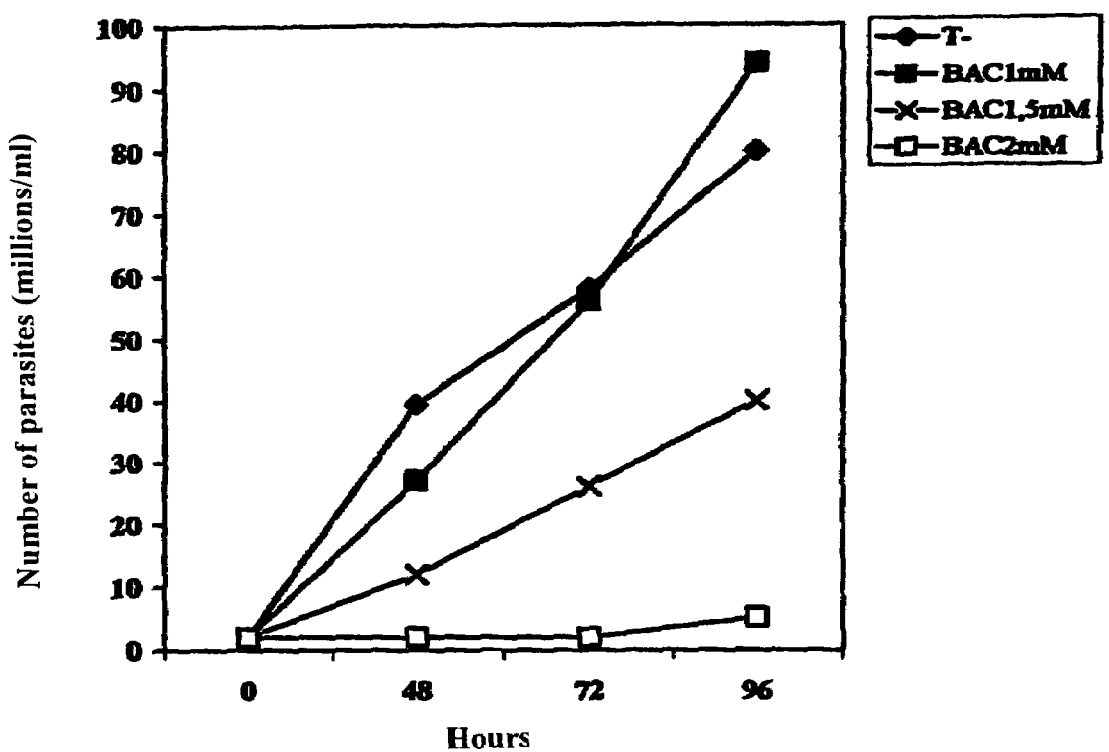

FIG. 9 shows the results of a parasite (L. major) growth inhibition test in a liquid medium using bacitracin. They are growth curves taken over 96 hours, for promastigotes of L major in the presence of 0, 1 mM, 1.5 mM or 2 mM of bacitracin.

Figure 10:
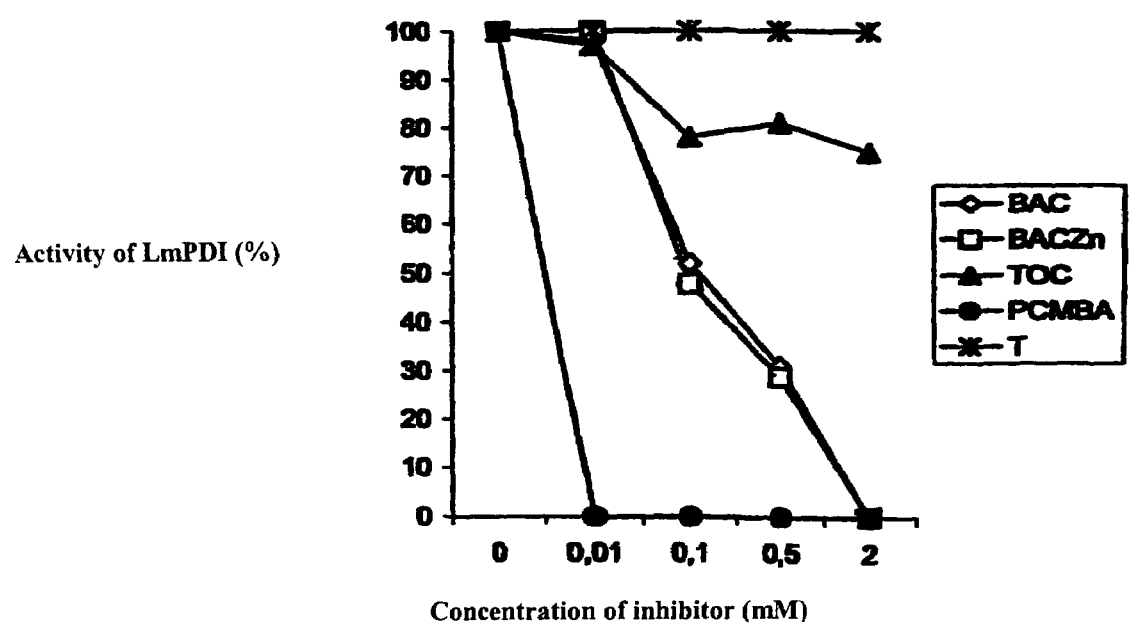

FIG. 10 shows the effect of bacitracin (BAC), zinc bacitracin (BACZn), p-chloromercuribenzoic acid (PCMBA) and tocinoic acid (TOC) on the in vitro activity of recombinant LmPDI. Different concentrations of inhibitors (0 to 2 mM) were used to follow the effect of PDI inhibitors on the capacity of LmPDI to reactivate scrambled RNase A in vitro. LmPDI without inhibitors was used as the positive control (T).

Figure 11:
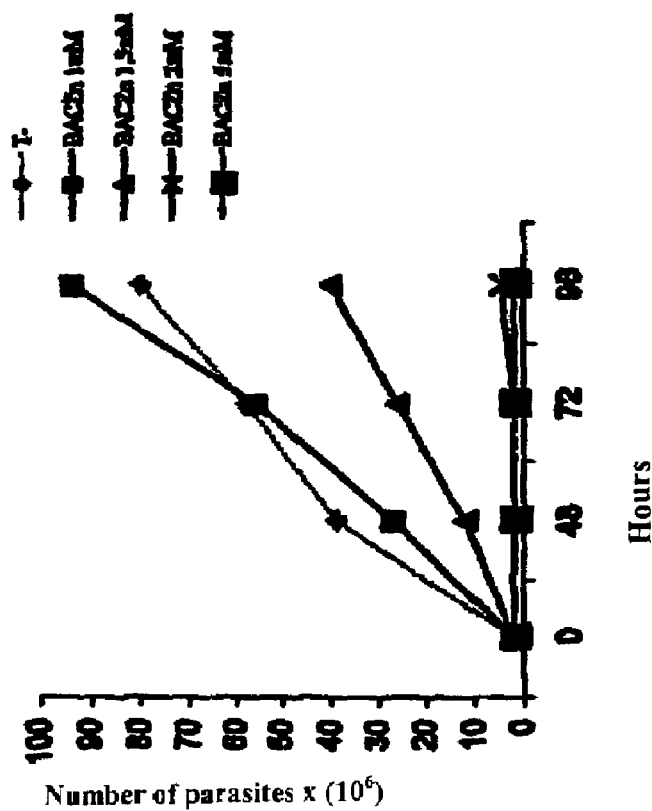
Figure 11:
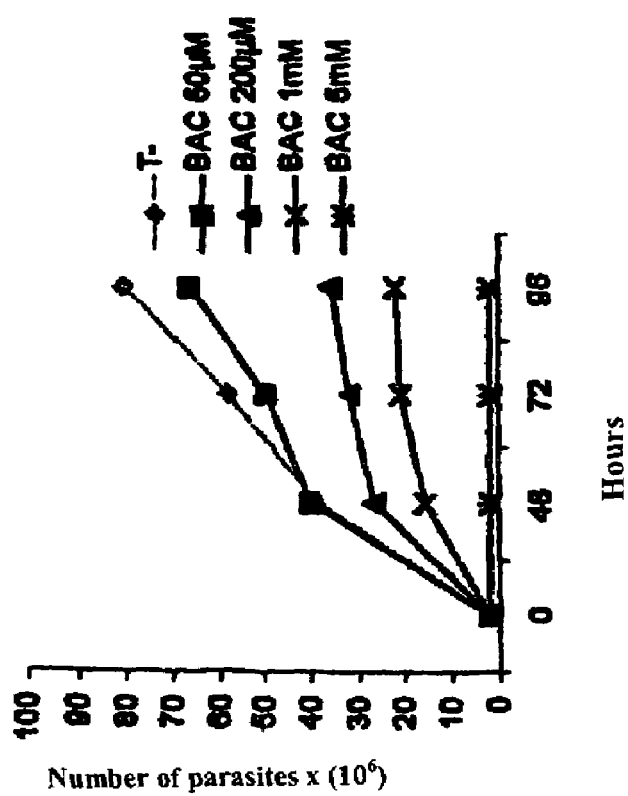
Figure 11:
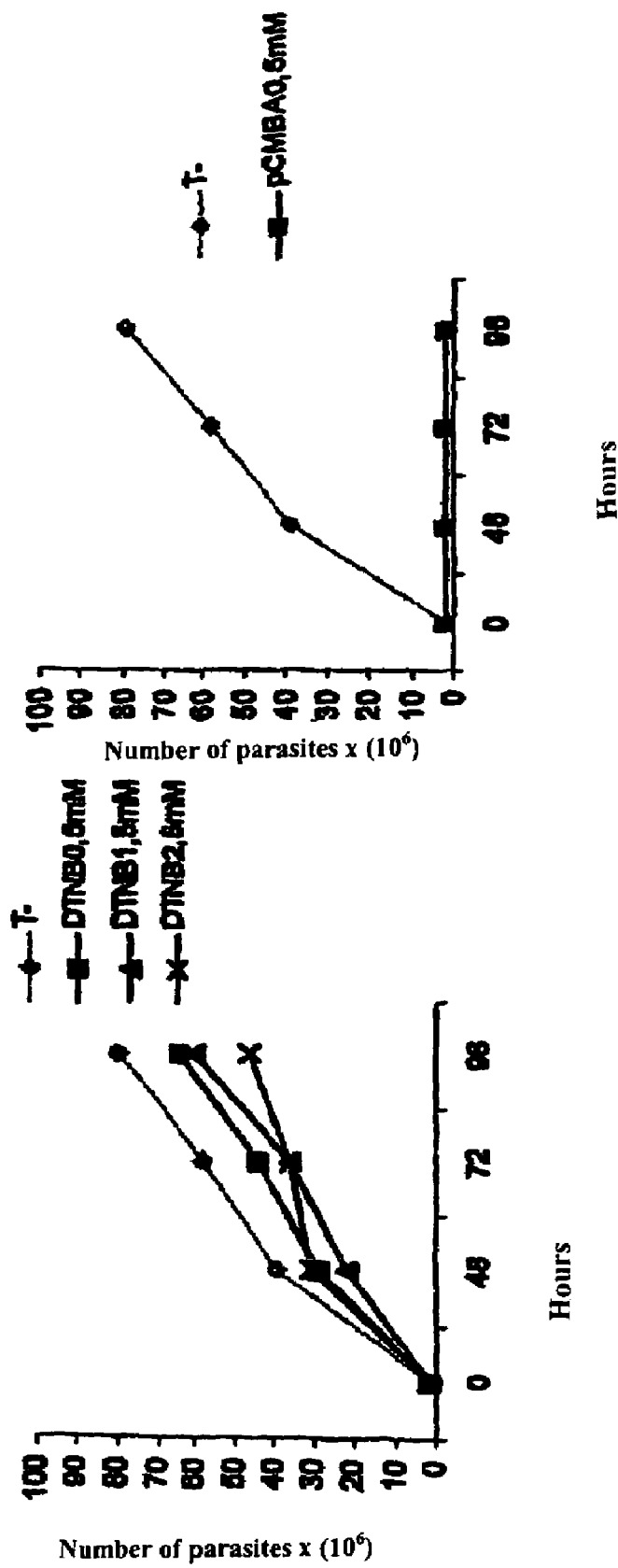

FIG. 11 shows the effect of bacitracin (BAC) (FIG. 11A), zinc bacitracin (BACZn) (FIG. 11B), 5,5'dithiobis-(2-nitrobenzoic acid) (DTNMB) (FIG. 11C) and p-chloromercuribenzoic acid (PCMBA) (FIG. 11D) on the in vitro growth of Leishmanias in a liquid medium. Different concentrations of inhibitors (0 to 5 mM) were used to follow the effect of PDI inhibitors on the multiplication of parasites in vitro. Parasites that had not been treated with inhibitors (T) were selected as a control for these experiments.

Figure 12:
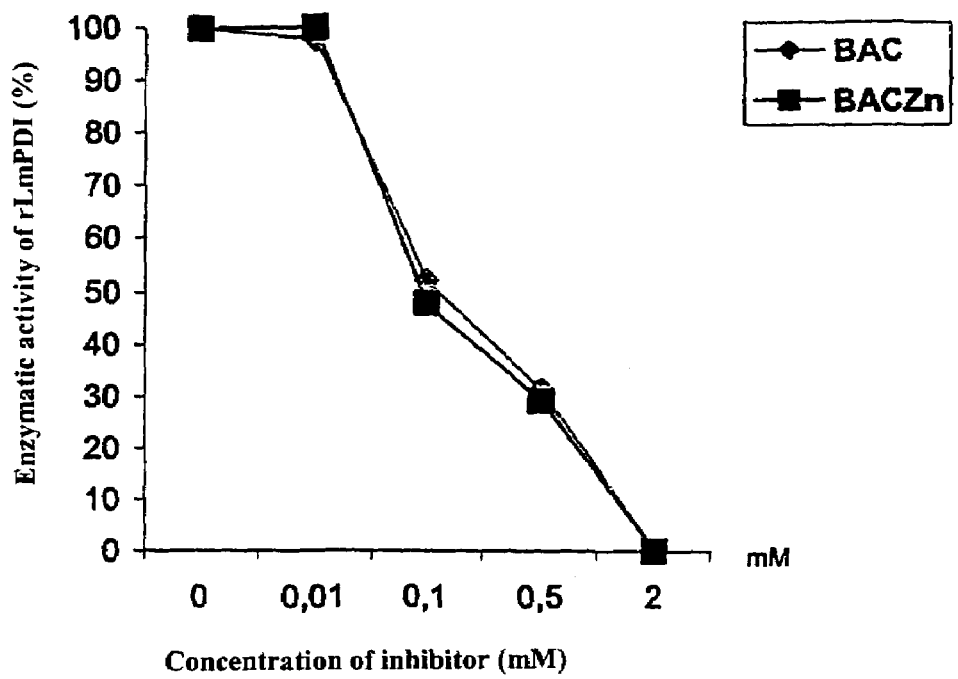

FIG. 12 shows the inhibition of the activity of rLmPDI by bacitracin and zinc bacitracin. The effect of bacitracin (BAC) and zinc bacitracin (BACZn) on the activity of rLmPDI was measured in vitro. Different concentrations of BAC and BACZn inhibitors (0 to 2 mM) were tested to analyze their effect on the capacity of rLmPDI to reactivate scrambled RNase in vitro. The activity of rLmPDI in the absence of inhibitors acted as a positive control.

Figure 13:
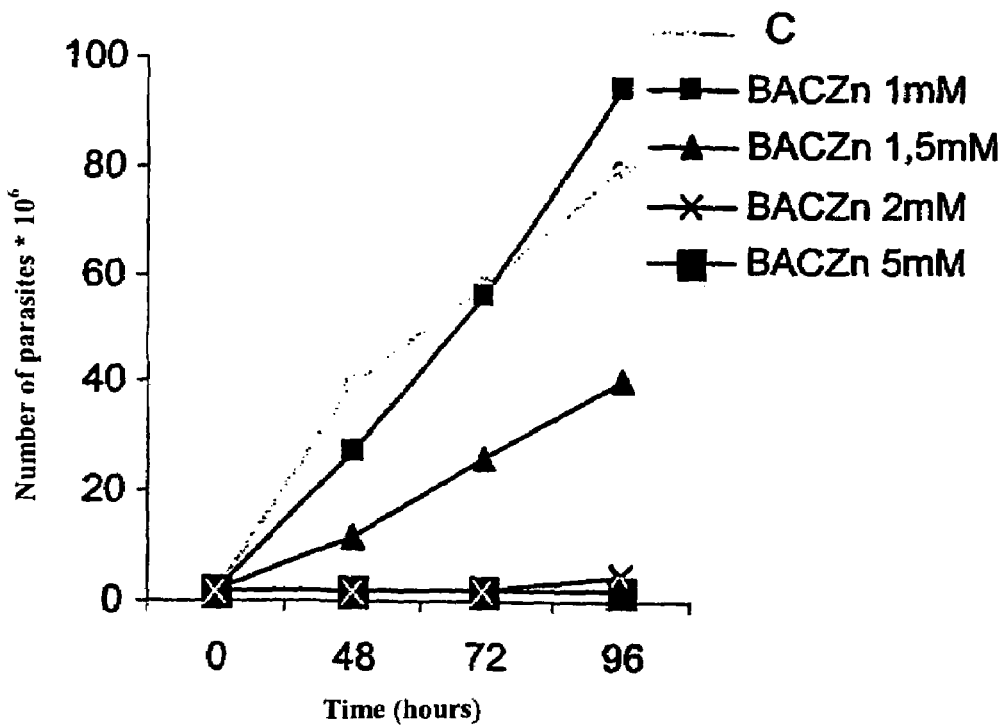

FIG. 13 illustrates the inhibition of the multiplication of GLC94 promastigotes by zinc bacitracin. The effect of zinc bacitracin (BACZn) on the multiplication of GLC94 promastogotes was determined in vitro. Different concentrations of inhibitor were tested to analyze their effect on the capacity of the parasites to multiply in vitro. The control (C) was constituted by parasites cultivated in a complete medium in the absence of inhibitors.

Figure 14:
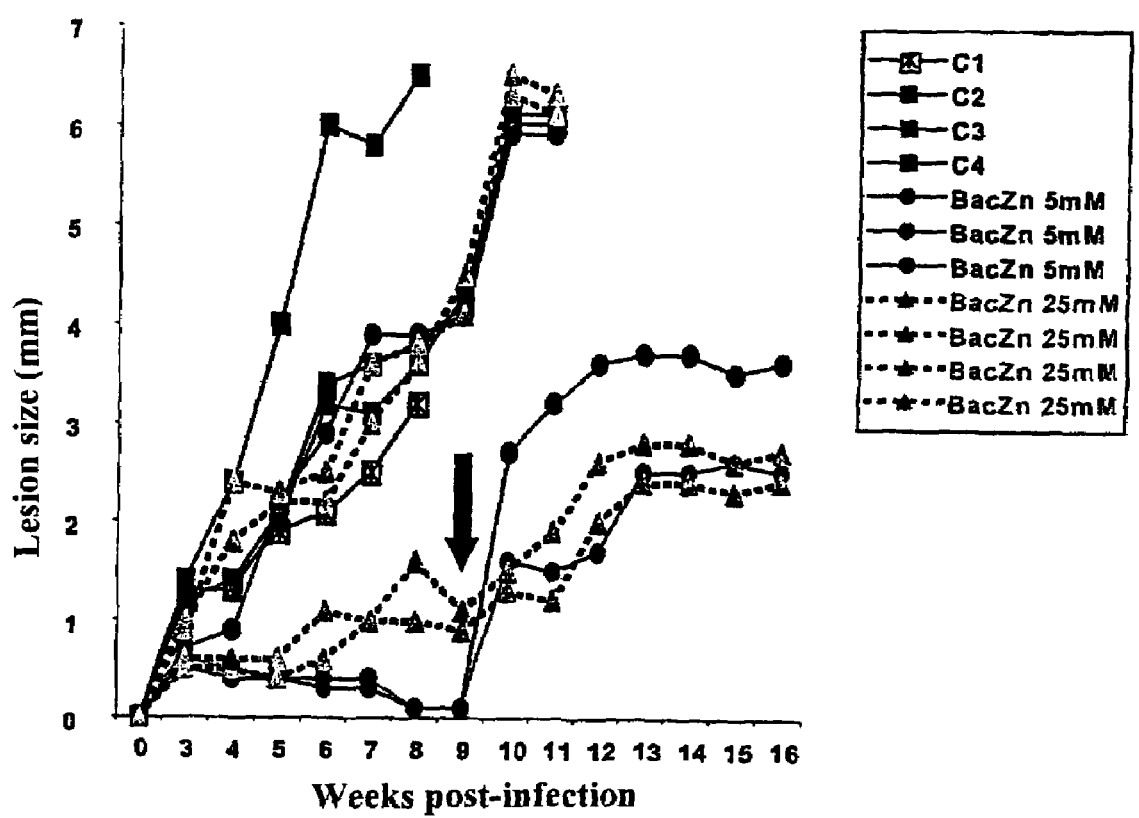

FIG. 14 shows the effect of zinc bacitracin on the evolution of the disease in sensitive BALB/c mice infected with GLC94 isolate promastigotes. Sensitive BALB/c mice were infected with $10^6$ promastigotes from the GLC94 isolate into the plantar pad and treated or not treated with bacitracin. The treatment was halted 9 weeks after infection (the arrow indicates treatment stoppage). Each curve shows the change in the size of a single mouse.

EXAMPLES

The experimental results shown in the following examples were obtained using the following materials and methods:

Parasites and Culture Conditions

The *L. major* isolates used in this study derived from human ZCL lesions obtained during the study summarized in Example 1. The parasites were cultivated in NNN medium (solid medium prepared and based on agarose and rabbit blood) at 26° C., and progressively transferred into RPMI (SIGMA, St Louis, Mo.) containing 2 mM of L-glutamine, 100 U/ml of penicillin, 100 µg/ml of streptomycin and 10% of deactivated fetal calf serum (complete medium). Promastigotes in the logarithmic growth phase were adjusted to $10^6$ parasites/ml in a constant volume of complete medium and incubated at 26° C. The stationary growth phase was reached after 4 to 6 days with the density of parasites of $3\times10^7$ to $8\times10^7$ parasites. Those promastigotes in the stationary growth phase were used for RNA and protein extractions.

RNA Extraction and Differential Display

Total RNA was extracted using the "TRIZOL™" reagent (a mono-phasic Solution of phenol and guandine isothiocyanate) (Gibco-BRL). PolyA+ RNA was purified by passage through an oligo dT/cellulose column using a "poly A+ RNA isolation kit" (Amersham-Pharmacia) following the manufacturer's instructions. 200 ng of mRNA were used in a reverse transcription reaction of 20 µl containing 1 µM of an oligo(dT)$_{11}$MN primer, with M=A or C or G and N=A or C or G or T (Genset), 1×First Strand Buffer (Gibco-BRL), 5 µM dNTP (Amersham-Pharmacia), 10 U of RNASIN™ (ribonuclease inhibitor) (Promega) and 200U of reverse transcriptase (Gibco-BRL).

After incubating at 37° C. for one hour, the reaction was stopped by incubating for 5 minutes at 95° C. The cDNA was amplified by PCR using a combination of 12 oligo dT and 10 arbitrary decamers. PCR was carried out in a volume of 20 µl containing 2 µl of reverse transcription reaction, 0.2 µM of 5' primer, 1 µM of 3' primer, 2 µM of dNTP, 10 µCi [$\alpha^{35}$S] of ATP, 1×Taq DNA polymerase reaction buffer and 1U of Taq polymerase (Amersham-Pharmacia). The reactions were incubated in a Perkin-Elmer 9600 thermocycler for 40 cycles at 94° C. for 30s, 40° C. for 60s and 72° C. for 30s followed by one cycle at 72° C. for 6 minutes. The PCR products were analyzed on a 6% acrylamide sequencing gel. The gel was vacuum dried on Whatmann 3MM paper and autoradiographed. The differentially expressed cDNA was excised from the gel, eluted and reamplified by PCR in the presence of the same oligonucleotides, under the conditions described above. The amplification products were cloned in pMOSblue vector using the Blunt-ended PCR cloning kit (Amersham Pharmacia), following the manufacturer's instructions. The cloned fragments were sequenced using a Sequencing Ready Reaction Kit (Perkin-Elmer) and analyzed using the ABI 377 automatic sequencer.

Northern Blot Analysis 200 ng of mRNA from promastigotes extracted during the stationary growth phase of 4 isolates from *L. major* were denatured, separated on a 1.2% agarose/2.2 M formaldehyde gel and transferred by capillarity on a "Hybond N+" (Amersham-Pharmacia) membrane. The nucleic acids were then fixed by heating for 2 hours at 80° C. The differentially expressed cDNA fragments and α-tubulin were labelled with [$\alpha^{32}$P]dCTP using the Megaprime DNA labelling system kit (Amersham-Pharmacia). Hybridizations were carried out in a 1×Denhardt's/6×SSC/0.1% SDS/0.1 mg.ml$^{-1}$ salmon sperm solution overnight at 65° C. The membranes were washed at 65° C. in a solution containing 0.1×SSC/0.1% SDS and autoradiographed.

Construction of a cDNA Library and Characterization of LmPDI cDNA

A cDNA library was constructed from 5 µg of mRNA from promastigotes from the most virulent strain (GLC94) in the ZAPII vector, following the manufacturer's instructions (Stratagene). 6×10$^6$ lysis plaques were screened using the p14 probe labeled with [$\alpha^{32}$P] dCTP using the Megaprime DNA labelling system kit (Amersham-Pharmacia). The lysis plaques of interest were removed and screened again to isolate positive clones from contaminating clones. The positive clones were then sequenced.

Southern Blot Analysis

Figure 5:
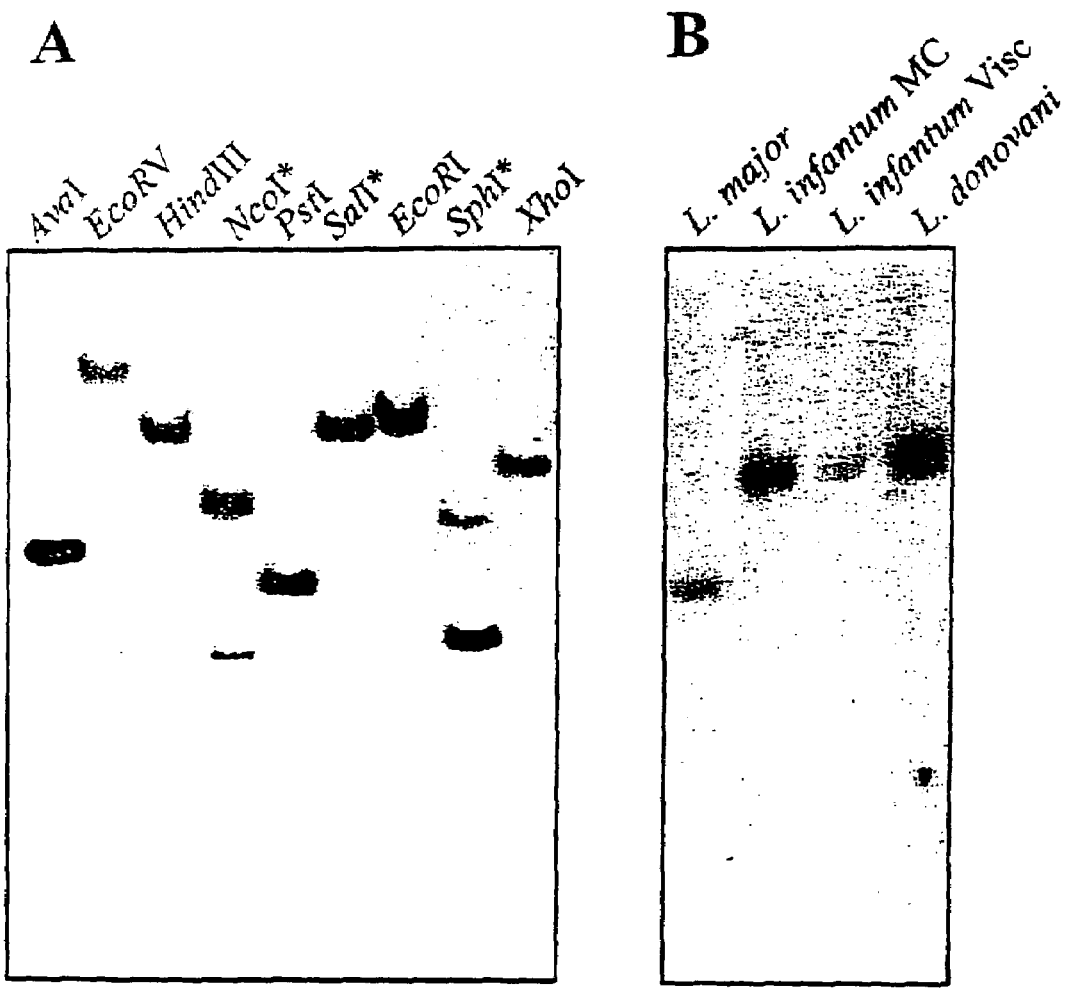

10 µg of genomic DNA extracted from promastigotes from the most virulent strain GLC94 were digested with the restriction enzymes indicated in FIG. 5 and analyzed on a 0.6% agarose gel, then transferred to a Hybond N+ (Amersham-Pharmacia) membrane. The membrane was incubated in the presence of a probe radioactively labeled with [$\alpha^{32}$P]dCTP and corresponding to the entire cDNA clone of LmPDI. The membranes were then washed in a solution containing 0.1× SSC/0.1% SDS and autoradiographed.

Expression and Purification of the Recombinant Protein LmPDI in *E. coli* BL21 Bacteria The sequence corresponding to the open reading frame of cDNA of LmPDI (1371 bp) deprived of the sequence coding for the peptide signal was cloned in the bacterial expression vector pET-22b (Novagen). *E. coli* BL21 bacteria containing the recombinant plasmid (pET-22b-LmPDI) were cultivated in LB medium then synthesis of the recombinant protein was induced in the presence of 1 mM of isopropyl-1-thio-D-galactopyranoside (IPTG) for 4 hours. The recombinant protein LmPDI-(His)$_6$ (SEQ ID No: 3) was purified by affinity chromatography on a nickel column (Ni$^{2+}$) (Amersham-Pharmacia). The purity of the protein produced was verified by SDS-PAGE.

Production of a Polyclonal Anti-LmPDI Antibody and Analysis of Expression of the Native Protein by Immunoblot A rabbit was immunized by intramuscular injection of 500 µg of emulsified purified recombinant LmPDI in incomplete Freund's adjuvant (IFA, Sigma) (v/v). The rabbit received two additional injections of 500 µg of recombinant protein, the first intramuscularly 15 days after the first injection and the second intradermally 30 days later. The rabbit was bled 10 days after the last injection; the serum was harvested and kept at −80° C. The protein lysate from the promastigotes was denatured in Laemmli 1×buffer for 10 minutes at 100° C., deposited on a 12% SDS-acrylamide gel and electrotransferred onto a nitrocellulose membrane (Millipore). The membranes were incubated in a saturated PBS/0.1% Tween20/3% skimmed milk solution at ambient temperature for one hour, then in the same solution containing anti-LmPDI antibody diluted to $1/1000^{th}$ at 4° C. overnight. After 3 washes in PBS/ 0.1% Tween20, the membranes were incubated in the presence of secondary rabbit anti-IgG antibody coupled with peroxidase (Amersham-Pharmacia, diluted to $1/1000$) for one hour at ambient temperature and washed 3 times in PBS/0.1% Tween20. The protein-antibody complexes were revealed by detecting the peroxidase activity using the "ECL system" kit, following the manufacturer's instructions (Amersham-Pharmacia).

Preparation of Scrambled RNase A 20 mg of purified ribonuclease (RNase A) was scrambled at ambient temperature for 18 hours in a buffer containing 0.15 M of DTT, 6 M of guanidine-HCl and 0.1 M of Tris-HCl at a pH of 8.6 before being purified on a Sephadex G-25 column equilibrated in 0.01 M HCl. The concentration of scrambled RNase A fractions was determined using an extinction coefficient of $9200 M^{-1} cm^{-1}$ at 275 nm. The fractions were stored at −80° C. for two weeks.

Reactivating RNase A in the Presence of Recombinant LmPDI Protein

Scrambled RNase A (8 µM) was incubated in a buffer containing 4.5 mM cCMP, 1 mM glutathione GSH, 0.2 mM glutathione disulfide GSSH, 2 mM EDTA and 100 mM of Tris-HCl pH 8 in the presence of bovine serum albumin (BSA) (1.4 µM) as a negative control, bovine protein disulfide-isomerase (1.4 µM) as a positive control, or recombinant LmPDI (1.4 µM) for 30 minutes at 25° C. RNase A reactivation was determined by measuring the RNase A activity at 296=m every 5 minutes, as described in the literature (Lyles and Gilbert, 1991).

Example 1

Selection of *L. major* Isolates Having Different Levels of Virulence

The *L. major* isolates used in this study derived from human ZCL lesions obtained during a prospective study carried out in 1994-1995 at El Guettar, in southern Tunisia (Louzir, Melby et al, 1998). They had been selected from 19 isolates on the basis of their pathogenic power during experimental infection of sensitive BALB/c mice: $2\times10^6$ amastigotes from various isolates were injected into the rear paw pads of BALB/c mice and the progress of the lesion was observed every week for 9 weeks. Five weeks after infection, the production of IL-4 and IFN-γ by mononuclear cells of lymphatic ganglia activated in vitro by antigens from the parasite was measured.

These experiments showed firstly the great heterogeneity in the progress of the disease induced by different isolates of *L. major* and secondly, that using a single isolate leads to reproducible results.

The most virulent strains induced the greatest amount of IL-4 and the lowest levels of IFN-γ in vitro, 5 weeks after infection.

From the observation that clinical expression of infection with *L. major* varies depending on the strains and is reproducible within each of them in the experimental model of infection of BALB/c sensitive mice, the inventors devised the hypothesis that the genes involved in virulence could be differentially expressed when comparing the most virulent isolates with the least virulent isolates. A preliminary analysis of the expression of a group of genes already described by other authors and associated with the virulence of the parasite, including LPG1, LPG2, KMP-11, Cpc, Cpb, Hsp100, Gene B and gp63, was carried out by a reverse transcription technique and quantitative gene amplification. This analysis did not show any difference between *L. major* isolates expressing a different pathogenicity in BALB/c mice (Kebaier, Louzir et al, 2001).

Two isolates, MHOM/TN/94/GLC94 and MHOM/TN/94/GLC67 (GLC94 and GLC67 respectively), which induced severe lesions, developed rapidly and represented the most virulent isolates, and 2 isolates MHOM/TN/94/GLC07 and MHOM/94/GLC32 (GLC07 and GLC32 respectively) inducing a less severe experimental disease and representing less virulent isolates, were selected to continue the search for virulence genes potentially expressed at different levels depending on the strains.

Example 2

Differential Display Identification of a Novel Protein Disulfide Isomerase LmPDI of *Leishmania major*, Involved in Natural Parasite Virulence 1—Identification of Genes Differentially Expressed in Virulent Isolates and Low Virulence Isolates of *L. major* mRNA was firstly purified from promastigotes from two highly virulent isolates (GLC94 and GLC67) and from two low virulence isolates (GLC32 and 07) then reverse transcribed to cDNA using Oligo$(dT)_{11}$MN primers, where M=A or C or G and N=A or C or G or T. The primer used during the differential display experiments was:

The amplification reactions were carried out by PCR using the same oligo-dT primers used during the reverse transcription reaction and combined with 10 arbitrary primers, as described in the scientific literature (Liang and Pardee, 1992; Liang, Bauer et al, 1995; Heard, Lewis et al, 1996).

In total, 60 combinations of primers were produced and analyzed. Polyacrylamide gel analysis of the amplification products using different combinations of primers showed that the genes from different isolates from *L. major*(highly virulent or low virulence) express, in approximately 95% of cases, the same mRNA and at equivalent levels. Taken alone, 25 messengers appear to be differentially expressed between highly virulent and low virulence isolates (FIG. 1A). The differentially expressed cDNA was firstly isolated from the acrylamide gel then reamplified using the same combinations of primer used during the first PCR and finally cloned in pMOS vector. Sequencing the different clones showed that a certain number of them were identified.

Analysis of the mRNA from the different isolates of *L. major* by Northern Blot using the 14 fragments differentially expressed as a probe showed that 3 clones out of the 14 isolates exhibit differential expression between highly virulent isolates and low virulence isolates. One of these clones, p14, has been characterized by Northern Blot. The probe corresponding to clone p14 specifically hybridized with a transcript with an approximate size of 2.2 kb, which is preferentially expressed in the two most virulent isolates compared with the two least virulent isolates (FIG. 1B). This confirms the results obtained by the Differential Display technique. Clone p14 has been completely sequenced and the size of this clone is 339 bp. A comparison of the nucleotide sequence of this fragment with the sequences described in the databases (GenBank and EMBL) did not identify a significantly homologous sequence. This could be due to the fact that the p14 clone corresponds to the non translated 3' terminal region of the messenger.

2—Cloning and Analysis of the Entire cDNA p14 Sequence

To isolate the entire cDNA sequence corresponding to the p14 clone, the 339 bp fragment was used to screen a cDNA bank of promastigotes of the GLC94 isolate. Two positive clones were isolated from $6 \times 10^5$ recombinant clones analyzed. FIG. 2 shows the nucleotide sequence of the longest clone, which is 2094 bp (SEQ ID No: 1). This clone has an open reading frame coding for a 477 amino acid (aa) polypeptide with a theoretical molecular weight of 52.4 kDa and an isoelectric point of 5.22. The N-terminal region of this protein corresponds to a potential peptide signal for export to the endoplasmic reticulum, 20 aa long. The non translated 5' region contains a splice leader sequence characteristic of Leishmanias and the non translated 3' region contains a poly A tail preceded by a potential polyadenylation site (FIG. 2).

The peptide sequence for the isolated clone showed 27-36% identity with proteins of the protein disulfide isomerase family (PDI and Erp) of several species (FIG. 3). Further, this protein contains two regions at residues 47-52 and 381-386 which are identical to the potential active sites (Cys-Gly-His-Cys, or CGHC) of PDI, Erp and proteins from the thioredoxin family. The C-terminal portion shows a potential signal for retention in the endoplasmic reticulum of the KDEL (EEDL) type at residues 474-477 suggesting that, like PDI and Erp, this protein is found in the cavity of the endoplasmic reticulum. P14 is thus a protein from the *L. major* protein disulfide isomerase family. It has been denoted LmPDI (FIGS. 2 and 3).

To determine whether LmPDI is endowed with an oxidoreductase thiodisulfide activity as demonstrated for the majority of the protein disulfide-isomerase described, the capacity of the recombinant protein LmPDI to renature denatured RNase A was studied. Recombinant LmPDI protein was synthesized in *E coli* than purified and used in a test, in vitro, for reactivating RNase. The results obtained show that LmPDI is capable of restoring RNase A activity in a similar manner to that of bovine PDI, used as a control (FIG. 4).

To identify the number of copies of the gene coding for LmPDI, the inventors carried out Southern Blot type hybridization using as a probe the cDNA fragment of $^{32}$P labeled LmPDI. The results obtained generally showed a single band, except for enzymes with a cleavage site within the cDNA of LmPDI (FIG. 5A). The gene coding for LmPDI is thus probably present in a single copy in the genome for *L. major*. Further, the gene for LmPDI appears to be conserved in different species of the *Leishmania* tested (*Leishmania* infantum, dermotropic, and a viscerotrope, *Leishmania donovani*) FIG. 5B).

3—Immunoblot Analysis of LmPDI Expression

To characterize the expression of the native protein, a rabbit was immunized with recombinant LmPDI protein synthesized in *E coli* and purified by affinity chromatography. Using immunoblot, the inventors have shown that the anti-LmPDI polyclonal antibody obtained strongly recognized a protein of the expected size (55 kDa) in lysates from promastigotes in the stationary growth phase of GLC94 (FIG. 6). Further, two other proteins were detected. The first had a molecular weight of 105 kDa, corresponding to about twice that of LmPDI, and the second had a molecular weight of 35 kDa. In order to verify whether the 105 kDa protein corresponded to a dimer of LmPDI, denatured GLC94 promastigote lysates were analyzed in the presence of high concentrations of DTT (0.5 mM). Under these conditions, the anti-LmPDI detected no more proteins of 105 kDa. These results suggest that LmPDI is organized into oligomers. The 35 kDa protein appears to be a contaminant. In fact, anti-LmPDI purified on an affinity column (Sepharose 4B-LmPDI) no longer recognizes the 35 kDa protein (FIG. 6).

In order to compare the level of expression of LmPDI between the most and the least virulent isolates, promastigote proteins were extracted then quantified in the stationary growth phase. 5 µg of proteins were analyzed on a 12% polyacrylamide-SDS gel and transferred to a nitrocellulose membrane. Western blot analysis using arm anti-LmPDI antibody showed that LmPDI (55 kDa) and its dimer (105 kDa) were more strongly expressed in the most virulent isolates (FIG. 7). In contrast, the 35 kDa contaminating protein was expressed in an equivalent manner regardless of the test strain. These results suggest a correlation between the level of expression of LmPDI and the pathogenic power of the studied isolates.

Example 3

Induction by LmPDI of In Vitro Proliferation of Mononuclear Cells from Individuals Having Active Lesions or ZCL Antecedents

*L. major* LmPDI, because of its high expression during the infectious stage of the parasite, could be a target for a cellular immune response. In order to verify the pertinence of this hypothesis, the capacity of LmPDI to induce a cellular immune response was evaluated by means of experiments on the proliferation of mononuclear cells obtained from individuals having active lesions or ZCL antecedents.

This study was carried out in 37 individuals living at El Guettar (southern Tunisia) for whom the results of the cellular proliferation test against total antigens from the parasite (SLA, a test indicating prior contact with the parasite) was available. These individuals were divided up as follows:

Group 1: composed of 8 individuals with a negative SLA test;

Group 2: composed of 29 individuals with a positive SLA test.

Mononuclear cells comprising lymphocytes and monocytes were separated from peripheral blood by centrifuging on a Ficoll/Hypaque gradient (Pharmacia, Uppsala, Sweden).

The results (FIG. 8) show significant proliferation with immune individuals.

Cytokines (IFN-β, IL-4) in PBMC culture supernatants were induced by incubating mononuclear cells for 48 hours with the same concentration of LmPDI and assaying by means of an ELISA test using human anti-IL-4 and anti-IFN-β monoclonal antibodies (Pharmingen, San Diego, Calif.).

The results came from a small sample of individuals. They clearly show the absence of IL-4 and the presence of significant amounts of IFN-β in the supernatant from cells stimulated by LmPDI.

This result shows an essentially type Th1 response, indicating that LmPDI could constitute a vaccine candidate against *Leishmania*.

Example 4

Inhibition of Growth of *Leishmania major* in a Liquid Medium in the Presence of a PDI Inhibitor Bacitracin is a known PDI inhibitor. Experiments using bacitracin showed that at the final concentration of 2 mM, bacitracin completely inhibited the growth of *L. major* parasites in a liquid medium (FIG. 9).

These experiments were carried out under the following experimental conditions:

a) Preparation of Scrambled RNase A:

20 mg of purified ribonuclease (RNase A) was reduced and denatured at ambient temperature for 18 hours in a buffer containing 0.15 M of DTT, 6M of guanidine-HCl and 0.1 M of Tris-HCl at a pH of 8.6, before being purified on a Sephadex G25 column equilibrated in 0.01 M HCl. The concentration of scrambled RNase A fractions was determined with the help of an extinction coefficient of 9200 $M^{-1}$ $cm^{-1}$ at 275 μm. The fractions were stored at −80° C. for two weeks.

b) Reactivation of RNase A in the Presence of Recombinant LmPDI Protein

The scrambled RNase A (8 μM) was incubated in a buffer containing 4.5 mM cCMP, 1 mM glutathione GSH, 0.2 mM glutathione disulfide GSSH, 2 mM EDTA and 100 mM Tris-HCl, pH 8, in the presence of bovine serum albumin (BSA) (1.4 μM) as a negative control, bovine protein disulfide-isomerase (1.4 μM) as a positive control, or recombinant LmPDI (1.4 μM) for 30 minutes at 25° C. RNase A reactivation was determined by measuring the RNase A activity at 296 nm every 5 minutes for 30 minutes as described in the literature (Lyles and Gilbert, 1991).

c) In Vitro Tests for Inhibition of the Thiodisulfide Oxido-Reductase Activity of Recombinant LmPDI by Different PDI Inhibitors The experimental conditions for the thio-disulfide oxido-reductase activity inhibition tests for recombinant LmPDI were strictly identical to those described in the paragraph "Reactivation of RNase A in the presence of recombinant LmPDI protein", except that the reactions were carried out in the presence of 0.01 mM, 0.1 mM, 0.5 mM and 2 mM of the following PDI inhibitors:

bacitracin;

zinc bacitracin;

p-chloromercuribenzoic acid (pCMBA);

tocinoic acid.

d) Inhibition of Parasite (*L. major*) Growth in a Liquid Medium

With the aim of determining the effect of bacitracin (BAC), zinc bacitracin (BACZn), p-chloromercuribenzoic acid (pCMBA) and 5,5'-dithiobis(2-nitrobenzoic acid) (DTNB) on the in vitro growth of Leishmanias in a liquid medium, different concentrations of the inhibitors cited above, 0 mM, 0.05 mM, 0.1 mM, 0.2 mM, 0.5 mM, 1 mM, 1.5 mM, 2 mM, 2.5 mM and 5 mM were added to RPMI supplemented with 5% fetal calf serum and containing $2\times10^6$/ml of parasites in the exponential growth phase. The parasites were incubated at 26° C. and counted every 24 hours over 96 hours. The parasites were counted on Mallassez cells.

Example 5

Evaluation of LmPDI Inhibiting Molecules as Regards their Capacities to Stop the Growth of *Leishmania major*

The evaluation of the role of LmPDI in *Leishmania* virulence allows novel strategies for identifying molecules that are active in treating *Leishmania* to be envisaged. It is probable that molecules known for their anti-PDI activities other than bacitracin are capable of inhibiting the growth of the parasite. An example of a protocol for evaluating molecules potentially effective against *Leishmania* is presented here.

An evaluation of molecules known for their anti-PDI activities or those which will be newly identified can be carried out in three steps. During the first step, the molecules are tested in vitro on recombinant LmPDI protein produced in *Escherichia (E.) coli*. Tests for inhibiting the growth of parasites in a liquid medium are then carried out and finally, the molecules are tested in the experimental murine model of leishmaniasis.

1—Evaluation of the Inhibition of Recombinant LmPDI.

The detailed technique for analyzing the PDI activity of LmPDI was described in Example 2 and in the Materials and Methods section above. The same technique can be used to evaluate the capacity of certain PDI inhibitors which are known or still to be identified (using a molecular model of LmPDI), by adding different concentrations of potential inhibitors to the reaction volume. The results are expressed as the percentage inhibition compared with the buffer alone. Only molecules with a significant and dose-dependent LmPDI inhibiting activity are retained.

With the aim of determining whether the different PDI inhibitors described in the literature could inhibit the thio-disulfide oxido-reductase activity of LmPDI, the capacity of these inhibitors to block the enzymatic activity of LmPDI synthesized in *E. coli* then purified was studied in an in vitro test, at different concentrations. The inhibitors were:

bacitracin;

zinc bacitracin;

p-chloromercuribenzoic acid (pCMBA);

tocinoic acid.

The results obtained are shown in FIG. 10 and show that the LmPDI activity is completely inhibited in the presence of 0.01 mM of pCMBA and 2 mM of bacitracin or zinc bacitracin. In contrast, tocinoic acid did not appear to have a very great effect on the activity of LmPDI at the concentrations employed (concentrations which completely inhibit the activity of human PDI).

2—Inhibition of the Growth of Parasites (*L. major*) in a Liquid Medium.

The test molecule was dissolved in a solvent the suitability of which depended on its physico-chemical properties (solubility in aqueous solutions or organic solvents). In all cases, the solvent alone was used as a control. As an example, the experiments could be carried out on the GLC94 *L. major* isolate. The composition of the culture medium was given above (Example 2 and Materials and Methods). The cultures were incubated at 26° C. and re-pricked out regularly to maintain the parasites in the stationary growth phase. For certain experiments, the amastigote-like stage of the parasite was used. In this case, the parasites (promastigotes) of the stationary growth phase were centrifuged, the medium was replaced with Schneider *Drosophila* medium adjusted to a pH of 5.0 and supplemented with fetal calf serum (FCS). The cultures were then incubated under 5% $CO_2$ at 35° C.

Inhibition of the growth of *L. major* promastigotes was carried out on parasites taken in the exponential growth phase, adjusted to the initial concentration of $10^6$ parasites/ml of complete medium and incubated in an amount of 100 µl/well in 96-well culture plates in the absence or presence of different concentrations of the test molecule. The parasites were incubated in 5% $CO_2$ at 26° C. and counted every 24 h for 96h. Parasite counting was carried out on a Mallassez cell. Alternatively, a hemocytometer could be used. All of the measurements were carried out in triplicate. The inhibiting capacity of a molecule was determined as the inhibiting concentration which reduces cell division by 50% compared with the control (IC50).

The reduction in the viability of amastigotes was evaluated using a fluorimetric test employing Almar Blue as a viability/growth indicator.

The PDI inhibitors described in paragraph (1-) were tested with the aim of evaluating their capacities to inhibit the in vitro growth of parasites. To this end, different quantities of inhibitors were added to RPMI containing $2 \times 10^6$/ml of parasites in the exponential growth phase. The parasites were incubated at 26° C. and counted every 24 hours over 96 hours. The parasites were counted on Mallassez cells. The results obtained are shown in FIG. 11 and show that bacitracin, zinc bacitracin or pCMBA completely inhibited the growth of *leishmania* in concentrations of 5 mM and 2 mM and 0.5 mM respectively. In contrast, 5,5'-dithiobis(2)nitrobenzoic acid) (DTNB) in the concentrations used (concentrations which completely inhibit the activity of human PDI) did not appear to have a very large effect on the growth of *Leishmanias*.

3—Evaluation Of the Efficacy of Pre-Selected Inhibitors in the Experimental Model of Infection of Sensitive BALB/c Mice by *L. major*.

The in vivo experiment will depend on the toxicity and physico-chemical properties of the test molecules. BALB/c mice will be infected by $10^6$ *L. major* promastigotes obtained during the stationary growth phase and injected (in a volume of 50 µl) into the plantar pad of the rear right paw. The lesion diameter will be measured weekly using sliding calipers.

In all, three therapeutic protocols will be applied depending on the case:
  for hydrophobic molecules, which diffuse well, and are slightly toxic or non-toxic, the product will be injected intraperitoneally at different concentrations and using different schemes. The frequency of injection will depend on the bioavailability of the molecule and on its half-life. In all cases, the protocol will be stopped at the end of 9 weeks following infection;
  for hydrosoluble and relatively toxic molecules, the injections will be made intra-lesionally (in general, the active doses can be divided by 10) by dint of at least four injections into the indurated zone;
  for liposoluble molecules, a pomade will be tested by weekly application to the experimental lesion.

Overall, and regardless of the mode of injecting the test product, two types of protocols will be carried out:
  a protocol which starts immediately after injecting the parasites;
  a protocol which starts 4 to 5 weeks after injecting parasites, at a time at which the lesion will already have been established.

In all cases, at the end of the protocol, the mice will be sacrificed and an estimate of the parasitic load will be made at the injection site and in the ganglion which drains the lesion.

Example 6

In Vitro Infection for Murine Macrophages by *Leishmania*

Murine bone marrow macrophages (MBMM) were obtained from bone marrow extruded from a femur or tibia from female BALB/c mice. The MBMM was cultivated in multi-chamber plates in an amount of $1.5 \times 10^3$ cells per well in 500 µl of complete medium. To stimulate the growth and maturation of the MBMM, the culture medium was supplemented with 20% of medium conditioned with L-929 fibroblasts as a source of macrophage colony stimulating factor (MCSF). After 6 days of culture at 37° C. and 5% $CO_2$, the medium was removed, the MBMM was washed, and fresh RPMI medium with 10% fetal calf serum but comprising no medium conditioned by L-929 fibroblasts was added. Intralesional amastigotes were purified from non-ulcerated lesions by differential centrifugation and counted using trypan blue viral stain. These parasites were used to infect the MBMM in a final ratio of four parasites per macrophage. Two hours after adding the parasites, the macrophages were washed five times with PBS to eliminate non phagocytary amastigotes. The cultures were then incubated at 37° C. in 95% air and 5% $CO_2$. The experiments were carried out at different points in time: 30 minutes and 2, 24 and 72 hours. At the indicated times, the wells were rinsed with PBS, the covers were removed and the infected macrophages were fixed with ethanol for 1 hour at ambient temperature. The plates were then washed and stained with Giemsa to follow the infection.

The infected macrophages were counted in the centre of each well were the cells were well spread out and the parasites could be counted easily. At this level of the plate, the parasite/macrophage ratio could be more than 4.

Example 7

Inhibition of the Enzymatic Activity of Recombinant LmPDI by Protein Disulfide-Isomerase Inhibitors Several protein disulfide-isomerase (PDI) inhibitors have been described in the literature (Ryser et al, 1994, Orlandi 1997, Mou et al, 1998). Of these, bacitracin and zinc bacitracin constitute a complex of polypeptide antibiotics produced by *Bacillus subtilis* and *Bacillus lichenformis*. Bacitracin A is the principal compound of commercial bacitracin, which is a mixture of at least nine bacitracins. This antibiotic is capable of inhibiting synthesis of the wall of many Gram+bacteria, but also the activity of many proteases such as PDI, transglutaminase, papain and neuropeptidase. The majority of those proteases have a cysteine residue in their active site.

In a first step, the investors tested the effect of these inhibitors in verifying their possible ability to alter the enzymatic activity of recombinant LmPDI (rLmPDI) in vitro.

The scrambled RNase technique described above (Lyles and Gilbert, 1991) was used to demonstrate the activity of LmPDI. Twenty milligrams of RNase A (Amersham-Pharmacia) was denatured in a buffer composed of 0.15 M dithiothreitol, 6M guanidine HCl and 0.1 M Tris-HCl, pH 8.6 for 18 hours at ambient temperature. The scrambled RNase was then purified on a Sephadex G25 column equilibrated in HCl 0.01 M and quantified by spectrophotometry at 275 nm.

In a glutathione-based reducing buffer, PDI catalyzes renaturing of scrambled RNase (Gilbert, 1998). Restoration of RNase activity was measured by spectrophotometry in the presence of cytidine 2'-3'-cyclic monophosphate (cCMP) as a substrate. 8 µM of scrambled RNase, alone or in the presence of 1.4 µM of bovine serum albumin (BSA) or 1.4 µM of rLmPDI was mixed in a buffer containing 4.5 mM of cCMP, 1 mM of reduced glutathione (GSH), 200 µM of oxidized glutathione (GSSG), 2 mM EDTA and 100 mM Tris-Cl, pH 8. The reaction was carried out at ambient temperature for 30 minutes. The hydrolysis of cCMP resulting from the renaturing of RNase was recorded by measuring the absorbance at 296 nm every 5 minutes for the half hour of the reaction.

The activity of the recombinant LmPDI (rLmPDI) was measured in the presence of different concentrations of bacitracin (BAC 0.01 mM-2 mM) and zinc bacitracin (BACZn, 0.01 mM-2 mM). The results are shown in FIG. 12.

These results show that bacitracin and zinc bacitracin have similar effects. In the presence of these two products, 50% inhibition was observed at 0.1 mM, 70% at 0.5 mM and 100% at 2 mM. The concentrations which inhibit rLmPDI are comparable with those described in the literature as inhibitors for PDIs from other species.

Example 8

In Vitro Growth Kinetics of *L. major* Promastigotes in the Presence of Zinc Bacitracin The inventors then tested the effect of zinc bacitracin on the in vitro growth kinetics of *L. major* promastigotes. For this study, only zinc bacitracin was tested, firstly because it had the same rLmPDI enzymatic activity inhibition profile as bacitracin, and secondly because bacitracin is more stable and less toxic when coupled with zinc.

To this end, promastigotes from the GLC94 isolate were cultured on a medium based on coagulated rabbit serum for two days. Then the parasites ($2 \times 10^6$ parasites per ml) were transferred into complete medium comprising zinc bacitracin BACZn, in concentrations of 1, 1.5 and 2.5 mM. Promastigotes cultured in complete medium in the absence of inhibitors were used as the control. Monitoring was by counting the parasites at 48, 72 and 96 hours. The results are shown in FIG. 13.

These results show that zinc bacitracin partially inhibits the growth of parasites at 1.5 mM with complete inhibition at 2 mM and at 5 mM, while it had no effect at 1 mM. Thus, it is very important to note that this molecule is capable of blocking the proliferation of *L. major* parasites in culture.

Example 9

Inhibition of the Growth of *L. major* Promastigotes in BALB/c Mice in the Presence of Zinc Bacitracin The availability of zinc bacitracin, which already forms a weapon in the therapeutic arsenal, has allowed it to be tested on the evolution of infection in the BALB/c mouse with *L. major*. Mice were infected with promastigotes in the stationary growth phase ($10^6$ promastigotes per paw) of the GLC94 isolate into the plantar pad of the rear paw and treated with a pomade based on 5 mM or 25 mM of BACZn (prepared in Vaseline). Treatment with the pomade was started 48 hours after injecting the parasites, by dint of one application per day over 5 days of the week. Mice infected in the same manner and treated with Vaseline were used as the control. The lesion size was measured each week. The results are shown in FIG. 14.

Although preliminary, these results show that zinc bacitracin attenuates the progress of the disease when it is applied locally in the form of a pomade, at the injection site, to BALB/c mice. It should be emphasized that in the group of treated mice, lesion attenuation was observed in 2 out of 3 mice treated with 5 mM bacitracin and 2 out of 4 mice treated with 25 mM bacitracin. Recurrence of the clinical disease after stopping the treatment was expected since BALB/c mice are incapable of completely eliminating the parasite and even the treatments used in man (glucantime and paramomycin) have little effect on the disease induced in the BALB/c mouse, in which complete disappearance of the parasites has never been observed.

LmPDI can thus be considered to be a potential target for anti-*leishmania* chemotherapy and it appears that bacitracin is potentially effective against *L. major*.

REFERENCES

Beverley, S. M. and S. J. Turco (1998). "Lipophosphoglycan (LPG) and the identification of virulence genes in the protozoan parasite *Leishmania*." *Trends Microbiol*(1): 35-40.

Chakrabarty, R., S. Mukherjee, et al. (1996). "Kinetics of entry of virulent and avirulent strains of *Leishmania donovani* into macrophages: a possible role of virulence molecules (gp63 and LPG)." *J Parasitol* 82(4): 632-5.

Cotrim, P. C., L. K. Garrity, et al. (1999). "Isolation of genes mediating resistance to inhibitors of nucleoside and ergosterol metabolism in *Leishmania* by overexpression/selection." *J Biol Chem* 274(53): 37723-30.

De, T. and S. Roy (1999). "Infectivity and attenuation of *Leishmania donovani* promastigotes: association of galactosyl transferase with loss of parasite virulence." *J Parasitol* 85(1):. 54-9.

Descoteaux, A., Y. Luo, et al. (1995). "A specialized pathway affecting virulence glycoconjugates of *Leishmania Science* 269(5232): 1869-72.

Desjardins, M. and A. Descoteaux (1997). "Inhibition of phagolysosomal biogenesis by the *Leishmania* lipophosphoglycan." *J Exp Med* 185(12): 2061-8.

Desjardins, M. and A. Descoteaux (1998). "Survival strategies of *Leishmania donovani* in mammalian host macrophages. *Res Immunol* 149(7-8): 689-92.

Dumas, C., M. Ouellette, et al. (1997). "Disruption of the trypanothione reductase gene of *Leishmania* decreases its ability to survive oxidative stress in macrophages." *Embo J* 16(10): 2590-8.

Ferrari, D. M. and H. D. Soling (1999). "The protein disulphide-isomerase family: unravelling a string of folds." *Biochem J* 339(Pt 1): 1-10.

Frand, A. R., J. W. Cuozzo, et al. (2000). "Pathways for protein disulphide bond formation." *Trends Cell Biol* 10(5): 203-10.

Garami, A. and T. Ilg (2001). "The role of phosphomannose isomerase in *Leishmania mexicana* glycoconjugate synthesis and virulence." *J. Biol Chem* 276(9): 6566-75.

Gilbert, H. F. (1998). "Protein disulfide isomerase." *Methods Enzymol* 290: 26-50.

Heard, P. L., C. S. Lewis, et al. (1996). "*Leishmania mexicana amazonensis*: differential display analysis and cloning of mRNAs from attenuated and infective forms." *J Eukarvot Microbiol* 43(5): 409-15.

Hubel, A., S. Krobitsch, et al. (1997). "*Leishmania major* Hsp100 is required chiefly in the mammalian stage of the parasite." *Mol Cell Biol* 17(10): 5987-95.

Hultgren, S. J., S. Abraham, et al. (1993). "Pilus and nonpilus bacterial adhesins: assembly and function in cell recognition." Cell 73(5): 887-901.

Ilg, T. (2000). "Proteophosphoglycans of Leishmania." Parasitol Today 16(11): 489-97.

Ilg, T., M. Demar, et al. (2001). "Phosphoglycan Repeat-deficient Leishmania mexicana Parasites Remain Infectious to Macrophages and Mice." J Biol Chem 276(7): 4988-97.

Kebaïer, C., H. Louzir, et al. (2001). "Heterogeneity of wild Leishmania major isolates in experimental murine pathogenicity and specific immune response." Infection and Immunity 69(8).

Khalil, E. A., A. M. E I Hassan, et al. (2000). "Autoclaved Leishmania major vaccine for prevention of visceral leishmaniasis: a randomised, double-blind, BCG-controlled trial in Sudan." Lancet 356(9241): 1565-9.

Liang, P., D. Bauer, et al. (1995). "Analysis of altered gene expression by differential display." Methods Enzymol 254: 304-21.

Liang, P. and A. B. Pardee (1992). "Differential display of eukaryotic messenger RNA by means of the polymerase chain reaction." Science 257(5072): 967-71.

Lira, R., S. Sundar, et al. (1999). "Evidence that the high incidence of treatment failures in Indian kala-azar is due to the emergence of antimony-resistant strains of Leishmania donovani." J Infect Dis 180(2): 564-7.

Louzir, H., P. C. Melby, et al. (1998). "Immunologic determinants of disease evolution in localized cutaneous leishmaniasis due to Leishmania major." J Infect Dis 177(6): 1687-95.

Lyles, M. M. and H. F. Gilbert (1991). "Catalysis of the oxidative folding of ribonuclease A by protein disulfide isomerase: dependence of the rate on the composition of the redox buffer." Biochemistry 30(3): 613-9.

Lyles, M. M. and H. F. Gilbert (1991). "Catalysis of the oxidative folding of ribonuclease A by protein disulfide isomerase: pre-steady-state kinetics and the utilization of the oxidizing equivalents of the isomerase." Biochemistry 30(3): 619-25.

Martin, J. L. (1995). "Thioredoxin—a fold for all reasons." Structure 3(3): 245-50.

McKerrow, J. H., J. C. Engel, et al. (1999). "Cysteine protease inhibitors as chemotherapy for parasitic infections." Bioorg Med Chem 7(4): 639-44.

Mottram, J. C., D. R. Brooks, et al. (1998). "Roles of cysteine proteinases of trypanosomes and Leishmania in host-parasite interactions." Curr. Opin Microbiol 1(4): 455-60.

Mottram, J. C., A. E. Souza, et al. (1996). "Evidence from disruption of the Imcpb gene array of Leishmania mexicana that cysteine proteinases are virulence factors." Proc Natl Acad Sci USA 93(12): 6008-13.

Mou, Y., H. Ni, et al. (1998). "The selective inhibition of beta 1 and beta 7 integrin-mediated lymphocyte adhesion by bacitracin." J Immunol 161(11): 6323-9.

Mukhopadhyay, S., P. Sen, et al. (1998). "Reduced expression of lipophosphoglycan (LPG) and kinetoplastid membrane protein (KMP)-11 in Leishmania donovani promastigotes in axenic culture." J. Parasitol 84(3): 644-7.

Noiva, R. (1999). "Protein disulfide isomerase: the multifunctional redox chaperone of the endoplasmic reticulum." Semin Cell Dev Biol 10(5): 481-93.

Orlandi, P. A. (1997). "Protein-disulfide isomerase-mediated reduction of the A subunit of cholera toxin in a human intestinal cell line." J. Biol. Chem 272(7): 4591-9.

Osterneier, M., K. De Sutter, et al. (1996). "Eukaryotic protein disulfide isomerase complements Escherichia coli dsbA mutants and increases the yield of a heterologous secreted protein with disulfide bonds." J Biol Chem 271 (18): 10616-22.

Paramchuk, W. J., S. O. Ismail, et al. (1997). "Cloning, characterization and overexpression of two iron superoxide dismutase cDNAs from Leishmania chagasi: role in pathogenesis." Mol Biochem Parasitol 90(1): 203-21.

Peek, J. A. and R. K. Taylor (1992). "Characterization of a periplasmic thiol:disulfide interchange protein required for the functional maturation of secreted virulence factors of Vibrio cholerae." Proc Natl Acad Sci USA 89(13): 62104.

Perez-Victoria, J. M., F. J. Perez-Victoria, et al. (2001). "High-affinity binding of silybin derivatives to the nucleotide-binding domain of a Leishmania tropica P-glycoprotein-like transporter and chemosensitization of a multidrug-resistant parasite to daunomycin." Antimicrob Agents Chemother 45(2): 439-46.

Ryser, H. J., E. M. Levy, et al. (1994). "Inhibition of human inmunodeficiency virus infection by agents that interfere with thiol-disulfide interchange upon virus-receptor interaction." Proc Natl Acad Sci USA 91(10): 4559-63.

Ryan, K. A., L. A. Garraway, et al. (1993). "Isolation of virulence genes directing surface glycosyl-phosphatidylinositol synthesis by functional complementation of Leishmania." Proc Natl Acad Sci USA 90(18): 8609-13.

Sacks, D. I., G. Modi, et al. (2000). "The role of phosphoglycars in Leislimania-sand fly interactions." Proc Natl Acad Sci USA 97(1): 406-11.

Selzer, P. M., X. Chen, et al. (1997). "Leishmania major: molecular modeling of cysteine proteases and prediction of new non peptide inhibitors." Exp Parasitol 87(3): 212-21.

Sharifi, I., A. R. FeKri, et al. (1998). "Randomised vaccine trial of single dose of killed Leishmania major plus BCG against anthroponotic cutaneous leishmaniasis in Bam, Iran." Lancet 351(9115): 1540-3.

Spath, G. F., L. Epstein, et al. (2000). "Lipophosphoglycan is a virulence factor distinct from related glycoconjugates in the protozoan parasite Leishmania major." Proc Natl Acad Sci USA 97(16): 9258-63.

Streit, J. A., T. J. Recker, et al. (2001). "Protective immunity against the protozoan Leishmania chagasi is induced by subclinical cutaneous infection with virulent but not avirulent organisms." J Immunol 66(3): 1921-9.

Titus, R. G., F. J. Gueiros-Filho, et al. (1995). "Development of a safe live leishmania vaccine line by gene replacement." Proc Natl Acad Sci USA 92(22): 10267-71.

Wang, Y., E. S. Bjes, et al. (2000). "Molecular aspects of complement-mediated bacterial killing. Periplasmic conversion of C9 from a protoxin to a toxin." J Biol Chem 275(7): 4687-92.

Wiese, M. (1998). "A mitogen-activated protein (MAP) kinase homologue of Leishmania mexicana is essential for parasite survival in the infected host." Embo J 17(9): 2619-28.

Yu, J. (1998). "Inactivation of DsbA, but not DsbC and DsbD, affects the intracellular survival and virulence of Shigella flexneri." Infect Immun 66(8): 3909-17.

Yu, J., B. Edwards-Jones, et al. (2000). "Key role for DsbA in cell-to-cell spread of Shigella flexneri, permitting secretion of Ipa proteins into interepithelial protrusions." Infect Immun 68(11): 6449-56.

Yu, J. and J. S. Kroll (1999). "DsbA: a protein-folding catalyst contributing to bacterial virulence." Microbes Infect 1(14): 1221-8.

Yu, J., H. Webb, et al. (1992). "A homologue of the Escherichia coli DsbA protein involved in disulphide bond formation is required for enterotoxin biogenesis in *Vibrio cholerae.*" *Mol Microbiol* 6(14): 1949-58.

Zhang, H. Z. and M. S. Donnenberg (1996). "DsbA is required for stability of the type IV pilin of enteropathogenic *escherichia coli.*" *Mol Microbiol* 21(4): 787-97.

Zhang, W. W. and G. Matlashewski (1997). "Loss of virulence in *Leishmania donovani* deficient in an amastigote-specific protein, A2." *Proc Natl Acad Sci USA* 94(16): 8807-11.

---

The invention claimed is:

1. An isolated or a purified protein of a *Leishmania* parasite, wherein the protein has SEQ ID NO:2.

2. A composition comprising the protein according to claim 1 and a pharmaceutically acceptable carrier therefor.

3. The isolated or purified protein of claim 1, wherein the isolated or purified protein is recombinantly expressed in a host cell.

* * * * *

SEQUENCE LISTING

```
<160> NUMBER OF SEQ ID NOS: 10

<210> SEQ ID NO 1
<211> LENGTH: 2094
<212> TYPE: DNA
<213> ORGANISM: Leishmania major
<220> FEATURE:
<221> NAME/KEY: CDS
<222> LOCATION: (241)..(1674)
<223> OTHER INFORMATION: LmPDI coding sequence (orf)

<400> SEQUENCE: 1
ggcaccagcg gcaccagagt tctgtactt tattgtcttt ctctattcta cccacacttg    60
cctctctgcg ctctctgtgc ctgtgcgggc gcgcaacgtg cctttctctc cgtattgccc   120
agctgtgagc tgctgcctac tggcaacgtg tacgccattc ccgtttcttg attctggtgc   180
agtgctcagc tctaccctat ttgtattgat accgttttcc ttttcgtttt gcaaagaaaa   240 atg cag cgc tca ttc ctt gtt ttt gtt ctg tgc gcc ctt ctc ttc tgc    288
Met Gln Arg Ser Phe Leu Val Phe Val Leu Cys Ala Leu Leu Phe Cys
  1               5                  10                  15 gtc gcg tcc gca gag gtg cag gtg gcc act aag gac aac ttt gac aag    336
Val Ala Ser Ala Glu Val Gln Val Ala Thr Lys Asp Asn Phe Asp Lys
             20                  25                  30 gtc gta atc ggg gat ctc acg ttg gtc aag ttt tat gct ccg tgg tgc    384
Val Val Ile Gly Asp Leu Thr Leu Val Lys Phe Tyr Ala Pro Trp Cys
         35                  40                  45 ggc cac tgc aag aca ctc gcc ccg gag ttt gta aag gcc gct gac atg    432
Gly His Cys Lys Thr Leu Ala Pro Glu Phe Val Lys Ala Ala Asp Met
     50                  55                  60 ctg gcc ggc atc gcg acc ctt gca gag gtc gat tgc acc aaa gaa gag    480
Leu Ala Gly Ile Ala Thr Leu Ala Glu Val Asp Cys Thr Lys Glu Glu
 65                  70                  75                  80 agc ctt gct gag aag tac gaa atc aag ggg ttc ccc acg ctg tac atc    528
Ser Leu Ala Glu Lys Tyr Glu Ile Lys Gly Phe Pro Thr Leu Tyr Ile
                 85                  90                  95 ttc cgt aac ggt gag aaa gtg aag atc tac gat ggt ccc cgc act gcc    576
Phe Arg Asn Gly Glu Lys Val Lys Ile Tyr Asp Gly Pro Arg Thr Ala
            100                 105                 110 gcc ggc atc gcg tcg tac atg aag gcg cat gtc ggt cca tcg atg aag    624
Ala Gly Ile Ala Ser Tyr Met Lys Ala His Val Gly Pro Ser Met Lys
        115                 120                 125 gcc atc tca acg gct gaa gag ctg gag gag ctc aag aag gag act ttc    672
Ala Ile Ser Thr Ala Glu Glu Leu Glu Glu Leu Lys Lys Glu Thr Phe
    130                 135                 140 ccg gtg tgc gtg gtg aag aca gcg agc acc gac tcg gag atg gcg tcg    720
Pro Val Cys Val Val Lys Thr Ala Ser Thr Asp Ser Glu Met Ala Ser
145                 150                 155                 160 atg ata acc aag gtg gcg gac tct ctc cgc tcg cag atg aac ttt gtg    768
Met Ile Thr Lys Val Ala Asp Ser Leu Arg Ser Gln Met Asn Phe Val
                165                 170                 175 ctc gtg acg gat gcg gcc atc tct ccg aat gat gcc atg gag tcg gtt    816
Leu Val Thr Asp Ala Ala Ile Ser Pro Asn Asp Ala Met Glu Ser Val
            180                 185                 190
```

```
acg gtg tat cgc aag aat gcg gag cgc gag gcg tac acc ggc gct aca      864
Thr Val Tyr Arg Lys Asn Ala Glu Arg Glu Ala Tyr Thr Gly Ala Thr
            195                 200                 205 cca atg acg gca gag tcg gtg aag agc ttt ctc acg agt gct gtg ttg      912
Pro Met Thr Ala Glu Ser Val Lys Ser Phe Leu Thr Ser Ala Val Leu
    210                 215                 220 gac tac ttt ggc gag ctc ggc cag gag agc ttt cag aag tac atg gaa      960
Asp Tyr Phe Gly Glu Leu Gly Gln Glu Ser Phe Gln Lys Tyr Met Glu
225                 230                 235                 240 gcg aac aag gat aaa cct ctt ggg tgg gtg ttc atc gac aag aac acg     1008
Ala Asn Lys Asp Lys Pro Leu Gly Trp Val Phe Ile Asp Lys Asn Thr
                245                 250                 255 gat tct gcg ttg aag ggg tca ctt gtg gcg gtg gcg gag aag tac cgc     1056
Asp Ser Ala Leu Lys Gly Ser Leu Val Ala Val Ala Glu Lys Tyr Arg
            260                 265                 270 tcg cag gtg ttg cta acc tac att gac ggc gat cag tac cgc ccc gtc     1104
Ser Gln Val Leu Leu Thr Tyr Ile Asp Gly Asp Gln Tyr Arg Pro Val
        275                 280                 285 tcg cgc cag ctg ggc att cct gag gat gcg aag ttc ccg gcg ttt gtg     1152
Ser Arg Gln Leu Gly Ile Pro Glu Asp Ala Lys Phe Pro Ala Phe Val
    290                 295                 300 gtc gat ttc gag cgc cgc cat cac gtg atg ggg acg gac acc cca gtc     1200
Val Asp Phe Glu Arg Arg His His Val Met Gly Thr Asp Thr Pro Val
305                 310                 315                 320 acc tcc gag tct gtc gct gcg ttt gtg gag aag tat gtc aag ggc gag     1248
Thr Ser Glu Ser Val Ala Ala Phe Val Glu Lys Tyr Val Lys Gly Glu
                325                 330                 335 acg aag cag acc gtg atg tcc gac gcg att ccc gct aag gag acg gtg     1296
Thr Lys Gln Thr Val Met Ser Asp Ala Ile Pro Ala Lys Glu Thr Val
            340                 345                 350 aac ggc ctc aca acg gtg gtg ggt cag act ttt gcg aag tac acg gac     1344
Asn Gly Leu Thr Thr Val Val Gly Gln Thr Phe Ala Lys Tyr Thr Asp
        355                 360                 365 ggc aca caa aac gtg atg ctg ctc ttc tac gcg ccg tgg tgc gga cac     1392
Gly Thr Gln Asn Val Met Leu Leu Phe Tyr Ala Pro Trp Cys Gly His
    370                 375                 380 tgc aag aag ctg cac ccc gtc tac gat aaa gta gcc aag agc ttc gag     1440
Cys Lys Lys Leu His Pro Val Tyr Asp Lys Val Ala Lys Ser Phe Glu
385                 390                 395                 400 tct gag aat gtg atc att gcg aag atg gat gcc acg acg aac gac ttt     1488
Ser Glu Asn Val Ile Ile Ala Lys Met Asp Ala Thr Thr Asn Asp Phe
                405                 410                 415 gac cgc gag aag ttt gag gtg tct gga ttt cca acg att tac ttc atc     1536
Asp Arg Glu Lys Phe Glu Val Ser Gly Phe Pro Thr Ile Tyr Phe Ile
            420                 425                 430 cca gcc ggc aag ccg cca atc gtg tac gag ggt ggc cgc acc gca gac     1584
Pro Ala Gly Lys Pro Pro Ile Val Tyr Glu Gly Gly Arg Thr Ala Asp
        435                 440                 445 gaa atc cag gtg ttt gtg aag tct cac ctg acc gcc tcc gcc gct cca     1632
Glu Ile Gln Val Phe Val Lys Ser His Leu Thr Ala Ser Ala Ala Pro
    450                 455                 460 tct ggc ggc cct tcc ggc aac agc gaa gag gaa gat ttg tag              1674
Ser Gly Gly Pro Ser Gly Asn Ser Glu Glu Glu Asp Leu
465                 470                 475 gactgcaagg gatgtggcgt ttataggctg ccctgccttc ccttgctgtt tctatgacgg   1734
attaggcttt ttttgtttat atgtggggtg gtcaagagag tgccagggct ccttctttat   1794
atccttgcgc tttctttat tttgcttcct tgtgttgacg tctatgcatg cgtgctgtcg   1854
acgactcttt gtcaacctgc gtcctatcta gtagcatcga tgtgaaaaga agagtagagg   1914
```

-continued

```
gaggtaacga tgcgtgcgct ggctgccgtt ttcatgggcg caatttcgag aaggaaaatc   1974
ggaaaatgga caggatagcg aaattagcgc aacgacaagg tcgtgcgtct ttctctatcg   2034
gtcattaaat ttctgggctt tgtaacaatg aaagaagtca cacaaaaaaa aaaaaaaaaa   2094

<210> SEQ ID NO 2
<211> LENGTH: 477
<212> TYPE: PRT
<213> ORGANISM: Leishmania major

<400> SEQUENCE: 2

Met Gln Arg Ser Phe Leu Val Phe Val Leu Cys Ala Leu Leu Phe Cys
 1               5                  10                  15

Val Ala Ser Ala Glu Val Gln Val Ala Thr Lys Asp Asn Phe Asp Lys
            20                  25                  30

Val Val Ile Gly Asp Leu Thr Leu Val Lys Phe Tyr Ala Pro Trp Cys
        35                  40                  45

Gly His Cys Lys Thr Leu Ala Pro Glu Phe Val Lys Ala Ala Asp Met
    50                  55                  60

Leu Ala Gly Ile Ala Thr Leu Ala Glu Val Asp Cys Thr Lys Glu Glu
65                  70                  75                  80

Ser Leu Ala Glu Lys Tyr Glu Ile Lys Gly Phe Pro Thr Leu Tyr Ile
                85                  90                  95

Phe Arg Asn Gly Glu Lys Val Lys Ile Tyr Asp Gly Pro Arg Thr Ala
            100                 105                 110

Ala Gly Ile Ala Ser Tyr Met Lys Ala His Val Gly Pro Ser Met Lys
        115                 120                 125

Ala Ile Ser Thr Ala Glu Glu Leu Glu Glu Leu Lys Lys Glu Thr Phe
    130                 135                 140

Pro Val Cys Val Val Lys Thr Ala Ser Thr Asp Ser Glu Met Ala Ser
145                 150                 155                 160

Met Ile Thr Lys Val Ala Asp Ser Leu Arg Ser Gln Met Asn Phe Val
                165                 170                 175

Leu Val Thr Asp Ala Ala Ile Ser Pro Asn Asp Ala Met Glu Ser Val
            180                 185                 190

Thr Val Tyr Arg Lys Asn Ala Glu Arg Glu Ala Tyr Thr Gly Ala Thr
        195                 200                 205

Pro Met Thr Ala Glu Ser Val Lys Ser Phe Leu Thr Ser Ala Val Leu
    210                 215                 220

Asp Tyr Phe Gly Glu Leu Gly Gln Glu Ser Phe Gln Lys Tyr Met Glu
225                 230                 235                 240

Ala Asn Lys Asp Lys Pro Leu Gly Trp Val Phe Ile Asp Lys Asn Thr
                245                 250                 255

Asp Ser Ala Leu Lys Gly Ser Leu Val Ala Val Ala Glu Lys Tyr Arg
            260                 265                 270

Ser Gln Val Leu Leu Thr Tyr Ile Asp Gly Asp Gln Tyr Arg Pro Val
        275                 280                 285

Ser Arg Gln Leu Gly Ile Pro Glu Asp Ala Lys Phe Pro Ala Phe Val
    290                 295                 300

Val Asp Phe Glu Arg Arg His His Val Met Gly Thr Asp Thr Pro Val
305                 310                 315                 320

Thr Ser Glu Ser Val Ala Ala Phe Val Glu Lys Tyr Val Lys Gly Glu
                325                 330                 335

Thr Lys Gln Thr Val Met Ser Asp Ala Ile Pro Ala Lys Glu Thr Val
```

```
                340                 345                 350
Asn Gly Leu Thr Thr Val Val Gly Gln Thr Phe Ala Lys Tyr Thr Asp
        355                 360                 365

Gly Thr Gln Asn Val Met Leu Leu Phe Tyr Ala Pro Trp Cys Gly His
    370                 375                 380

Cys Lys Lys Leu His Pro Val Tyr Asp Lys Val Ala Lys Ser Phe Glu
385                 390                 395                 400

Ser Glu Asn Val Ile Ile Ala Lys Met Asp Ala Thr Thr Asn Asp Phe
                405                 410                 415

Asp Arg Glu Lys Phe Glu Val Ser Gly Phe Pro Thr Ile Tyr Phe Ile
            420                 425                 430

Pro Ala Gly Lys Pro Pro Ile Val Tyr Glu Gly Gly Arg Thr Ala Asp
        435                 440                 445

Glu Ile Gln Val Phe Val Lys Ser His Leu Thr Ala Ser Ala Ala Pro
    450                 455                 460

Ser Gly Gly Pro Ser Gly Asn Ser Glu Glu Asp Leu
465                 470                 475

<210> SEQ ID NO 3
<211> LENGTH: 467
<212> TYPE: PRT
<213> ORGANISM: Artificial sequence
<220> FEATURE:
<223> OTHER INFORMATION: Description of artificial sequence: recombinant
      protein

<400> SEQUENCE: 3

Met Ala Glu Val Gln Val Ala Thr Lys Asp Asn Phe Asp Lys Val Val
1               5                   10                  15

Ile Gly Asp Leu Thr Leu Val Lys Phe Tyr Ala Pro Trp Cys Gly His
            20                  25                  30

Cys Lys Thr Leu Ala Pro Glu Phe Val Lys Ala Ala Asp Met Leu Ala
        35                  40                  45

Gly Ile Ala Thr Leu Ala Glu Val Asp Cys Thr Lys Glu Glu Ser Leu
    50                  55                  60

Ala Glu Lys Tyr Glu Ile Lys Gly Phe Pro Thr Leu Tyr Ile Phe Arg
65                  70                  75                  80

Asn Gly Glu Lys Val Lys Ile Tyr Asp Gly Pro Arg Thr Ala Ala Gly
                85                  90                  95

Ile Ala Ser Tyr Met Lys Ala His Val Gly Pro Ser Met Lys Ala Ile
            100                 105                 110

Ser Thr Ala Glu Glu Leu Glu Glu Leu Lys Lys Glu Thr Phe Pro Val
        115                 120                 125

Cys Val Val Lys Thr Ala Ser Thr Asp Ser Glu Met Ala Ser Met Ile
    130                 135                 140

Thr Lys Val Ala Asp Ser Leu Arg Ser Gln Met Asn Phe Val Leu Val
145                 150                 155                 160

Thr Asp Ala Ala Ile Ser Pro Asn Asp Ala Met Glu Ser Val Thr Val
                165                 170                 175

Tyr Arg Lys Asn Ala Glu Arg Glu Ala Tyr Thr Gly Ala Thr Pro Met
            180                 185                 190

Thr Ala Glu Ser Val Lys Ser Phe Leu Thr Ser Ala Val Leu Asp Tyr
        195                 200                 205

Phe Gly Glu Leu Gly Gln Glu Ser Phe Gln Lys Tyr Met Glu Ala Asn
    210                 215                 220
```

```
Lys Asp Lys Pro Leu Gly Trp Val Phe Ile Asp Lys Asn Thr Asp Ser
225                 230                 235                 240

Ala Leu Lys Gly Ser Leu Val Ala Val Ala Glu Lys Tyr Arg Ser Gln
            245                 250                 255

Val Leu Leu Thr Tyr Ile Asp Gly Asp Gln Tyr Arg Pro Val Ser Arg
        260                 265                 270

Gln Leu Gly Ile Pro Glu Asp Ala Lys Phe Pro Ala Phe Val Val Asp
    275                 280                 285

Phe Glu Arg Arg His His Val Met Gly Thr Asp Thr Pro Val Thr Ser
290                 295                 300

Glu Ser Val Ala Ala Phe Val Glu Lys Tyr Val Lys Gly Glu Thr Lys
305                 310                 315                 320

Gln Thr Val Met Ser Asp Ala Ile Pro Ala Lys Glu Thr Val Asn Gly
            325                 330                 335

Leu Thr Thr Val Val Gly Gln Thr Phe Ala Lys Tyr Thr Asp Gly Thr
        340                 345                 350

Gln Asn Val Met Leu Leu Phe Tyr Ala Pro Trp Cys Gly His Cys Lys
    355                 360                 365

Lys Leu His Pro Val Tyr Asp Lys Val Ala Lys Ser Phe Glu Ser Glu
370                 375                 380

Asn Val Ile Ile Ala Lys Met Asp Ala Thr Thr Asn Asp Phe Asp Arg
385                 390                 395                 400

Glu Lys Phe Glu Val Ser Gly Phe Pro Thr Ile Tyr Phe Ile Pro Ala
            405                 410                 415

Gly Lys Pro Pro Ile Val Tyr Glu Gly Gly Arg Thr Ala Asp Glu Ile
        420                 425                 430

Gln Val Phe Val Lys Ser His Leu Thr Ala Ser Ala Ala Pro Ser Gly
    435                 440                 445

Gly Pro Ser Gly Asn Ser Glu Glu Glu Asp Leu Leu Glu His His His
450                 455                 460

His His His
465

<210> SEQ ID NO 4
<211> LENGTH: 497
<212> TYPE: PRT
<213> ORGANISM: T. brucei

<400> SEQUENCE: 4

Met Arg Ala Ile Phe Leu Val Ala Leu Ala Leu Ala Thr Met Arg Glu
1               5                   10                  15

Ser Thr Ala Glu Ser Leu Lys Leu Thr Lys Glu Asn Phe Asn Glu Thr
            20                  25                  30

Ile Ala Lys Ser Glu Ile Phe Leu Val Lys Phe Tyr Val Asp Thr Cys
        35                  40                  45

Gly Tyr Cys Gln Met Leu Ala Pro Glu Trp Glu Lys Ala Ala Asn Glu
    50                  55                  60

Thr Ile Asp Asn Ala Leu Met Gly Glu Val Asp Cys His Ser Gln Pro
65                  70                  75                  80

Glu Leu Ala Ala Asn Phe Ser Ile Arg Gly Tyr Pro Thr Ile Ile Leu
            85                  90                  95

Phe Arg Asn Gly Lys Glu Ala Glu His Tyr Gly Gly Ala Arg Thr Lys
        100                 105                 110

Asp Asp Ile Ile Lys Tyr Ile Lys Ala Asn Val Gly Pro Ala Val Thr
    115                 120                 125
```

-continued

```
Pro Ala Ser Asn Ala Glu Glu Val Thr Arg Ala Lys Glu Glu His Asp
        130                 135                 140

Val Val Cys Val Gly Leu Thr Ala Asn Asn Ser Thr Ser Leu Ser Thr
145                 150                 155                 160

Thr Leu Ala Glu Ala Ala Gln Ser Phe Arg Val Ser Leu Lys Phe Phe
                165                 170                 175

Glu Ala Glu Pro Lys Leu Phe Pro Asp Glu Lys Pro Gly Thr Ile Val
            180                 185                 190

Val Tyr Arg Lys Gly Gly Glu Lys Glu Val Tyr Asp Gly Pro Met Glu
        195                 200                 205

Val Glu Lys Leu Thr Glu Phe Leu Gln Ile Ser Arg Val Ala Phe Gly
    210                 215                 220

Gly Glu Ile Thr Pro Glu Asn Tyr Gln Tyr Ser Val Ile Lys Arg
225                 230                 235                 240

Pro Val Gly Trp Ala Met Val Lys Pro Asn Glu Thr Ala Ser Ile Glu
                245                 250                 255

Leu Lys Glu Ser Leu Thr Glu Val Gly Lys Lys Met Arg Ser His Met
            260                 265                 270

Val Val Leu Trp Val Asn Ile Ser Lys His Pro Val Trp Arg Asp Phe
        275                 280                 285

Gly Val Pro Glu Asp Ala Lys Tyr Pro Ala Phe Leu Ala Ile His Trp
    290                 295                 300

Gly Ala Asn Tyr Leu His Ser Thr Ala Glu Val Val Thr Arg Glu Ser
305                 310                 315                 320

Leu Glu Lys Phe Ile Leu Glu Phe Ala Ala Gly Arg Val Glu Pro Thr
                325                 330                 335

Ile Lys Ser Leu Pro Val Pro Glu Val Glu Thr Val Asp Gly Lys Thr
            340                 345                 350

Thr Ile Val Ala Lys Thr Met Gln Lys His Leu Thr Ser Gly Lys Asp
        355                 360                 365

Met Leu Ile Leu Phe Phe Ala Pro Trp Cys Gly His Cys Lys Asn Phe
    370                 375                 380

Ala Pro Thr Phe Asp Lys Ile Ala Lys Glu Phe Asp Ala Thr Asp Leu
385                 390                 395                 400

Ile Val Ala Glu Leu Asp Ala Thr Ala Asn Tyr Val Asn Ser Ser Thr
                405                 410                 415

Phe Thr Val Thr Ala Phe Pro Thr Val Phe Phe Val Pro Asn Gly Gly
            420                 425                 430

Lys Pro Val Val Phe Glu Gly Glu Arg Ser Phe Glu Asn Val Tyr Glu
        435                 440                 445

Phe Val Arg Lys His Val Thr Thr Phe Lys Val Ser Glu Lys Pro Ala
    450                 455                 460

Asn Val Thr Glu Glu Lys Lys Ser Glu Glu Asn Lys Ser Ser Lys
465                 470                 475                 480

Ser Asn Glu Ser Asn Asp Ser Asn Glu Ser Asn Val Asp Lys Gln Asp
                485                 490                 495

Leu

<210> SEQ ID NO 5
<211> LENGTH: 502
<212> TYPE: PRT
<213> ORGANISM: H. jecorina

<400> SEQUENCE: 5
```

```
Met Gln Gln Lys Arg Leu Thr Ala Ala Leu Val Ala Ala Leu Ala Ala
 1               5                  10                  15

Val Val Ser Ala Glu Ser Asp Val Lys Ser Leu Thr Lys Asp Thr Phe
            20                  25                  30

Asn Asp Phe Ile Asn Ser Asn Asp Leu Val Leu Ala Glu Ser Phe Ala
            35                  40                  45

Pro Trp Cys Gly His Cys Lys Ala Leu Ala Pro Glu Tyr Glu Glu Ala
        50                  55                  60

Ala Thr Thr Leu Lys Asp Lys Ser Ile Lys Leu Ala Lys Val Asp Cys
 65                  70                  75                  80

Val Glu Glu Ala Asp Leu Cys Lys Glu His Gly Val Glu Gly Tyr Pro
                85                  90                  95

Thr Leu Lys Val Phe Arg Gly Leu Asp Lys Val Ala Pro Tyr Thr Gly
            100                 105                 110

Pro Arg Lys Ala Asp Gly Ile Thr Ser Tyr Met Val Lys Gln Ser Leu
        115                 120                 125

Pro Ala Val Ser Ala Leu Thr Lys Asp Thr Leu Glu Asp Phe Lys Thr
        130                 135                 140

Ala Asp Lys Val Val Leu Val Ala Tyr Ile Ala Ala Asp Asp Lys Ala
145                 150                 155                 160

Ser Asn Glu Thr Phe Thr Ala Leu Ala Asn Glu Leu Arg Asp Thr Tyr
            165                 170                 175

Leu Phe Gly Gly Val Asn Asp Ala Ala Val Ala Glu Ala Glu Gly Val
            180                 185                 190

Lys Phe Pro Ser Ile Val Leu Tyr Lys Ser Phe Asp Glu Gly Lys Asn
        195                 200                 205

Val Phe Ser Glu Lys Phe Asp Ala Glu Ala Ile Arg Asn Phe Ala Gln
        210                 215                 220

Val Ala Ala Thr Pro Leu Val Gly Glu Val Gly Pro Glu Thr Tyr Ala
225                 230                 235                 240

Gly Tyr Met Ser Ala Gly Ile Pro Leu Ala Tyr Ile Phe Ala Glu Thr
            245                 250                 255

Ala Glu Glu Arg Glu Asn Leu Ala Lys Thr Leu Lys Pro Val Ala Glu
            260                 265                 270

Lys Tyr Lys Gly Lys Ile Asn Phe Ala Thr Ile Asp Ala Lys Asn Phe
        275                 280                 285

Gly Ser His Ala Gly Asn Ile Asn Leu Lys Thr Asp Lys Phe Pro Ala
        290                 295                 300

Phe Ala Ile His Asp Ile Glu Lys Asn Leu Lys Phe Pro Phe Asp Gln
305                 310                 315                 320

Ser Lys Glu Ile Thr Glu Lys Asp Ile Ala Ala Phe Val Asp Gly Phe
            325                 330                 335

Ser Ser Gly Lys Ile Glu Ala Ser Ile Lys Ser Glu Pro Ile Pro Glu
            340                 345                 350

Thr Gln Glu Gly Pro Val Thr Val Val Ala His Ser Tyr Lys Asp
            355                 360                 365

Ile Val Leu Asp Asp Lys Lys Asp Val Leu Ile Glu Phe Tyr Thr Pro
        370                 375                 380

Trp Cys Gly His Cys Lys Ala Leu Ala Pro Lys Tyr Asp Glu Leu Ala
385                 390                 395                 400

Ser Leu Tyr Ala Lys Ser Asp Phe Lys Asp Lys Val Val Ile Ala Lys
            405                 410                 415
```

```
Val Asp Ala Thr Ala Asn Asp Val Pro Asp Glu Ile Gln Gly Phe Pro
            420                 425                 430

Thr Ile Lys Leu Tyr Pro Ala Gly Asp Lys Lys Asn Pro Val Thr Tyr
            435                 440                 445

Ser Gly Ala Arg Thr Val Glu Asp Phe Ile Glu Phe Ile Lys Glu Asn
450                 455                 460

Gly Lys Tyr Lys Ala Gly Val Glu Ile Pro Ala Glu Pro Thr Glu Glu
465                 470                 475                 480

Ala Glu Ala Ser Glu Ser Lys Ala Ser Glu Glu Ala Lys Ala Ser Glu
            485                 490                 495

Glu Thr His Asp Glu Leu
            500

<210> SEQ ID NO 6
<211> LENGTH: 488
<212> TYPE: PRT
<213> ORGANISM: C. elegans

<400> SEQUENCE: 6

Met Ile Trp Val Gln Ala Ala Leu Val Ala Ser Phe Leu Ala Phe Ala
  1               5                  10                  15

Ser Ala Gly Gly Ala Val Leu Glu Tyr Thr Asp Gly Asn Phe Asp Asp
                 20                  25                  30

Leu Ile Gln Thr His Asp Ile Ala Leu Val Lys Phe Tyr Ala Pro Trp
             35                  40                  45

Cys Gly His Cys Lys Lys Ile Ala Pro Glu Tyr Glu Arg Ala Ala Pro
         50                  55                  60

Lys Leu Ala Ser Asn Asp Pro Pro Val Ala Leu Val Lys Val Asp Cys
 65                  70                  75                  80

Thr Thr Glu Lys Thr Val Cys Asp Lys Phe Gly Val Lys Gly Phe Pro
                 85                  90                  95

Thr Leu Lys Ile Phe Arg Asn Gly Val Pro Ala Gln Asp Tyr Asp Gly
            100                 105                 110

Pro Arg Asp Ala Asp Gly Ile Val Lys Phe Met Arg Gly Gln Ser Gly
        115                 120                 125

Pro Ser Ser Lys Glu Leu Lys Thr Val Ala Glu Phe Glu Lys Phe Thr
    130                 135                 140

Gly Gly Asp Glu Asn Val Val Ile Gly Phe Phe Glu Ser Glu Ser Lys
145                 150                 155                 160

Leu Lys Asp Ser Tyr Leu Lys Val Ala Asp Thr Glu Arg Asp Arg Phe
                165                 170                 175

Ser Phe Ala His Thr Ser Asn Lys Asp Ile Ile Lys Lys Ala Gly Tyr
            180                 185                 190

Ser Asp Asp Val Val Val Phe Val Pro Lys Lys Leu His Asn Lys Phe
        195                 200                 205

Asp Thr Asn Glu Phe Lys Tyr Asp Gly Asn Tyr Thr Asp Lys Ile
    210                 215                 220

Lys Asn Phe Leu Val His Glu Thr Val Gly Phe Ala Gly Ile Arg Thr
225                 230                 235                 240

Gln Gly Asn Leu Phe Gln Phe Glu Gln Lys Pro Ile Val Ile Val Tyr
                245                 250                 255

Tyr Asn Val Asp Tyr Val Lys Asp Pro Lys Gly Ser Asn Tyr Trp Arg
            260                 265                 270

Asn Arg Val Leu Lys Val Ala Gln Asn Tyr Lys Arg Lys Val Gln Phe
        275                 280                 285
```

```
Ala Val Ser Asn Lys Glu Glu Phe Ser Ser Glu Ile Glu Thr Asn Gly
            290                 295                 300

Leu Gly Glu Arg Lys Asp Ser Asp Lys Pro Ile Val Ala Ile Leu Thr
305                 310                 315                 320

Asn Glu Gly Lys Tyr Pro Met Asp Gln Glu Phe Ser Val Asp Asn Leu
                    325                 330                 335

Gln Gln Phe Val Asp Glu Val Leu Ala Gly Asn Ala Glu Pro Tyr Met
                340                 345                 350

Lys Ser Glu Pro Ile Pro Asp Glu Gln Gly Asp Val Lys Val Ala Val
            355                 360                 365

Gly Lys Asn Phe Lys Glu Leu Ile Met Asp Ala Asp Lys Asp Val Leu
370                 375                 380

Ile Glu Phe Tyr Ala Pro Trp Cys Gly His Cys Lys Ser Leu Ala Pro
385                 390                 395                 400

Lys Tyr Glu Glu Leu Ala Glu Lys Leu Asn Lys Glu Asp Val Ile Ile
                405                 410                 415

Ala Lys Met Asp Ala Thr Ala Asn Asp Val Pro Pro Met Phe Glu Val
                420                 425                 430

Arg Gly Phe Pro Thr Leu Phe Trp Leu Pro Lys Asn Ala Lys Ser Asn
                435                 440                 445

Pro Ile Pro Tyr Asn Gly Gly Arg Glu Val Lys Asp Phe Val Ser Phe
            450                 455                 460

Ile Ser Lys His Ser Thr Asp Gly Leu Lys Gly Phe Ser Arg Asp Gly
465                 470                 475                 480

Lys Lys Lys Lys Lys Thr Glu Leu
                485

<210> SEQ ID NO 7
<211> LENGTH: 532
<212> TYPE: PRT
<213> ORGANISM: C. reinhard

<400> SEQUENCE: 7

Met Asn Arg Trp Asn Leu Leu Ala Leu Thr Leu Gly Leu Leu Leu Val
1               5                   10                  15

Ala Ala Pro Phe Thr Lys His Gln Phe Ala His Ala Ser Asp Glu Tyr
                20                  25                  30

Glu Asp Asp Glu Glu Asp Ala Pro Ala Ala Pro Lys Asp Asp Asp
            35                  40                  45

Val Asp Val Thr Val Val Thr Val Lys Asn Trp Asp Glu Thr Val Lys
        50                  55                  60

Lys Ser Lys Phe Ala Leu Val Glu Phe Tyr Ala Pro Trp Cys Gly His
65                  70                  75                  80

Cys Lys Thr Leu Lys Pro Glu Tyr Ala Lys Ala Thr Ala Leu Lys
                85                  90                  95

Ala Ala Ala Pro Asp Ala Leu Ile Ala Lys Val Asp Ala Thr Gln Glu
                100                 105                 110

Glu Ser Leu Ala Gln Lys Phe Gly Val Gln Gly Tyr Pro Thr Leu Lys
            115                 120                 125

Trp Phe Val Asp Gly Glu Leu Ala Ser Asp Tyr Asn Gly Pro Arg Asp
        130                 135                 140

Ala Asp Gly Ile Val Gly Trp Val Lys Lys Thr Gly Pro Pro Ala
145                 150                 155                 160

Val Thr Val Glu Asp Ala Asp Lys Leu Lys Ser Leu Glu Ala Asp Ala
```

-continued

```
                    165                 170                 175
Glu Val Val Val Gly Tyr Phe Lys Ala Leu Glu Gly Glu Ile Tyr
                180                 185                 190

Asp Thr Phe Lys Ser Tyr Ala Ala Lys Thr Glu Asp Val Phe Val
            195                 200                 205

Gln Thr Thr Ser Ala Asp Val Ala Lys Ala Ala Gly Leu Asp Ala Val
        210                 215                 220

Asp Thr Val Ser Val Val Lys Asn Phe Ala Gly Glu Asp Arg Ala Thr
225                 230                 235                 240

Ala Val Leu Ala Thr Asp Ile Asp Thr Asp Ser Leu Thr Ala Phe Val
                245                 250                 255

Lys Ser Glu Lys Met Pro Pro Thr Ile Glu Phe Asn Gln Lys Asn Ser
                260                 265                 270

Asp Lys Ile Phe Asn Ser Gly Ile Asn Lys Gln Leu Ile Leu Trp Thr
            275                 280                 285

Thr Ala Asp Asp Leu Lys Ala Asp Ala Glu Ile Met Thr Val Phe Arg
        290                 295                 300

Glu Ala Ser Lys Lys Phe Lys Gly Gln Leu Val Phe Val Thr Val Asn
305                 310                 315                 320

Asn Glu Gly Asp Gly Ala Asp Pro Val Thr Asn Phe Phe Gly Leu Lys
                325                 330                 335

Gly Ala Thr Ser Pro Val Leu Leu Gly Phe Phe Met Glu Lys Asn Lys
                340                 345                 350

Lys Phe Arg Met Glu Gly Glu Phe Thr Ala Asp Asn Val Ala Lys Phe
            355                 360                 365

Ala Glu Ser Val Val Asp Gly Thr Ala Gln Ala Val Leu Lys Ser Glu
        370                 375                 380

Ala Ile Pro Glu Asp Pro Tyr Glu Asp Gly Val Tyr Lys Ile Val Gly
385                 390                 395                 400

Lys Thr Val Glu Ser Val Val Leu Asp Glu Thr Lys Asp Val Leu Leu
                405                 410                 415

Glu Val Tyr Ala Pro Trp Cys Gly His Cys Lys Lys Leu Glu Pro Ile
                420                 425                 430

Tyr Lys Lys Leu Ala Lys Arg Phe Lys Lys Val Asp Ser Val Ile Ile
            435                 440                 445

Ala Lys Met Asp Gly Thr Glu Asn Glu His Pro Glu Ile Glu Val Lys
        450                 455                 460

Gly Phe Pro Thr Ile Leu Phe Tyr Pro Ala Gly Ser Asp Arg Thr Pro
465                 470                 475                 480

Ile Val Phe Glu Gly Gly Asp Arg Ser Leu Lys Ser Leu Thr Lys Phe
                485                 490                 495

Ile Lys Thr Asn Ala Lys Ile Pro Tyr Glu Leu Pro Lys Lys Gly Ser
            500                 505                 510

Asp Gly Asp Glu Gly Thr Ser Asp Asp Lys Asp Lys Pro Ala Ser Asp
        515                 520                 525

Lys Asp Glu Leu
    530
```

<210> SEQ ID NO 8
<211> LENGTH: 496
<212> TYPE: PRT
<213> ORGANISM: D. melano

<400> SEQUENCE: 8

-continued

```
Met Lys Phe Leu Ile Cys Ala Leu Phe Leu Ala Ala Ser Tyr Val Ala
 1               5                  10                  15

Ala Ser Ala Glu Ala Glu Val Lys Val Glu Gly Val Leu Val Ala
            20                  25                  30

Thr Val Asp Asn Phe Lys Gln Leu Ile Ala Asp Asn Glu Phe Val Leu
            35                  40                  45

Val Glu Phe Tyr Ala Pro Trp Cys Gly His Cys Lys Ala Leu Ala Pro
        50                  55                  60

Glu Tyr Ala Lys Ala Ala Gln Gln Leu Ala Glu Lys Glu Ser Pro Ile
65                  70                  75                  80

Lys Leu Ala Lys Val Asp Ala Thr Val Glu Gly Leu Ala Glu Gln
                85                  90                  95

Tyr Ala Val Arg Gly Tyr Pro Thr Leu Lys Phe Phe Arg Ser Gly Ser
                100                 105                 110

Pro Val Glu Tyr Ser Gly Gly Arg Gln Ala Ala Asp Ile Ile Ala Trp
        115                 120                 125

Val Thr Lys Lys Thr Gly Pro Pro Ala Lys Asp Leu Thr Ser Val Ala
        130                 135                 140

Asp Ala Glu Gln Phe Leu Lys Asp Asn Glu Ile Ala Ile Gly Phe
145                 150                 155                 160

Phe Lys Asp Leu Glu Ser Glu Glu Ala Lys Thr Phe Thr Lys Val Ala
                165                 170                 175

Asn Ala Leu Asp Ser Phe Val Phe Gly Val Ser Ser Asn Ala Asp Val
            180                 185                 190

Ile Ala Lys Tyr Glu Ala Lys Asp Asn Gly Val Val Leu Phe Lys Pro
        195                 200                 205

Phe Asp Asp Lys Lys Ser Val Phe Glu Gly Glu Leu Asn Glu Glu Asn
    210                 215                 220

Leu Lys Lys Phe Ala Gln Val Gln Ser Leu Pro Leu Ile Val Asp Phe
225                 230                 235                 240

Asn His Glu Ser Ala Ser Lys Ile Phe Gly Gly Ser Ile Lys Ser His
                245                 250                 255

Leu Leu Phe Phe Val Ser Arg Glu Gly His Ile Glu Lys Tyr Val
            260                 265                 270

Asp Pro Leu Lys Glu Ile Ala Lys Lys Tyr Arg Asp Asp Ile Leu Phe
        275                 280                 285

Val Thr Ile Ser Ser Asp Glu Glu Asp His Thr Arg Ile Phe Glu Phe
        290                 295                 300

Phe Gly Met Asn Lys Glu Glu Val Pro Thr Ile Arg Leu Ile Lys Leu
305                 310                 315                 320

Glu Glu Asp Met Ala Lys Tyr Lys Pro Glu Ser Asp Asp Leu Ser Ala
                325                 330                 335

Glu Thr Ile Glu Ala Phe Leu Lys Lys Phe Leu Asp Gly Lys Leu Lys
            340                 345                 350

Gln His Leu Leu Ser Gln Glu Leu Pro Glu Asp Trp Asp Lys Asn Pro
        355                 360                 365

Val Lys Val Leu Val Ser Ser Asn Phe Glu Ser Val Ala Leu Asp Lys
        370                 375                 380

Ser Lys Ser Val Leu Val Glu Phe Tyr Ala Pro Trp Cys Gly His Cys
385                 390                 395                 400

Lys Gln Leu Ala Pro Ile Tyr Asp Gln Leu Ala Glu Lys Tyr Lys Asp
                405                 410                 415

Asn Glu Asp Ile Val Ile Ala Lys Met Asp Ser Thr Ala Asn Glu Leu
```

-continued

```
                   420             425             430
Glu Ser Ile Lys Ile Ser Ser Phe Pro Thr Ile Lys Tyr Phe Arg Lys
            435                 440                 445

Glu Asp Asn Lys Val Ile Asp Phe Asn Leu Asp Arg Thr Leu Asp Asp
450                 455                 460

Phe Val Lys Phe Leu Asp Ala Asn Gly Glu Val Ala Asp Ser Glu Pro
465                 470                 475                 480

Val Glu Glu Thr Glu Glu Glu Glu Ala Pro Lys Lys Asp Glu Leu
                485                 490                 495

<210> SEQ ID NO 9
<211> LENGTH: 481
<212> TYPE: PRT
<213> ORGANISM: C. parvum

<400> SEQUENCE: 9

Met Ile Gly Ile Arg Ser Leu Val Ser Ala Ala Phe Leu Gly Phe Ser
 1               5                  10                  15

Cys Leu Ser Lys Val Val Leu Gly Gly Asp Glu Ala His Phe Ile Ser
             20                  25                  30

Glu His Ile Thr Ser Leu Thr Ser Ser Asn Phe Glu Asp Phe Ile Lys
         35                  40                  45

Ser Lys Glu His Val Ile Val Thr Phe Phe Ala Pro Trp Cys Gly His
     50                  55                  60

Cys Thr Ala Leu Glu Pro Glu Phe Lys Ala Thr Cys Ala Glu Ile Ser
 65                  70                  75                  80

Lys Leu Ser Pro Pro Val His Cys Gly Ser Val Asp Ala Thr Glu Asn
                 85                  90                  95

Met Glu Leu Ala Gln Gln Tyr Gly Val Ser Gly Tyr Pro Thr Ile Lys
            100                 105                 110

Phe Phe Ser Gly Ile Asp Ser Val Gln Asn Tyr Ser Gly Ala Arg Ser
        115                 120                 125

Lys Asp Ala Phe Ile Lys Tyr Ile Lys Lys Leu Thr Gly Pro Ala Val
    130                 135                 140

Gln Val Ala Glu Ser Glu Glu Ala Ile Lys Thr Ile Phe Ala Ser Ser
145                 150                 155                 160

Ser Ser Ala Phe Val Gly Arg Phe Thr Ser Lys Asp Ser Ala Glu Tyr
                165                 170                 175

Ala Val Phe Glu Lys Val Ala Ser Gly His Arg Glu His Asn Tyr Ala
            180                 185                 190

Phe Ile Ala Phe Phe Gln Glu Gly Glu Gln Lys Leu Glu Val Leu His
        195                 200                 205

Lys Asp Glu Glu Pro Val Ser Leu Pro Met Pro Lys Thr Val Glu Glu
    210                 215                 220

Leu Glu Ala Lys Ile Ser Ile Met Asn Val Pro Leu Phe Ser Ala Ile
225                 230                 235                 240

Ser Ala Glu Asn Tyr Ser Leu Tyr Met Ser Arg Glu Gly Tyr Thr Pro
                245                 250                 255

Gly Ser Val Val Leu Thr Arg Thr Ser Pro Ser Met Leu Gln Thr Leu
            260                 265                 270

Glu Arg Leu Gln Leu Ile Thr Glu Lys Ser Met Pro Leu Phe Ser Leu
        275                 280                 285

Asp Thr Glu Gln Phe Gly Ser His Ala Thr Gln His Leu Leu Ile Glu
    290                 295                 300
```

```
Lys Phe Pro Gly Leu Val Ile Gln Ser Val Asn Val Pro Ser Ile Arg
305                 310                 315                 320

Tyr Met Tyr Gly Pro Ala Lys Phe Asp Ser Val Glu Pro Leu Lys Glu
            325                 330                 335

Phe Met Lys Gln Val Ser Glu Gly Lys His Glu Leu Ser Ile Lys Ser
            340                 345                 350

Glu Pro Ile Pro Ala Glu Gln Ser Gly Pro Val Thr Val Val Gly
            355                 360                 365

Lys Thr Phe Glu Glu Ile Val Phe Arg Ser Asp Lys Asp Val Leu Leu
370                 375                 380

Glu Ile Tyr Ala Gln Trp Cys Gly His Cys Lys Asn Leu Glu Pro Ile
385                 390                 395                 400

Tyr Asn Gln Leu Gly Glu Glu Tyr Lys Asp Asn Asp Lys Val Val Ile
                405                 410                 415

Ala Lys Ile Asn Gly Pro Gln Asn Asp Ile Pro Tyr Glu Gly Phe Ser
            420                 425                 430

Pro Arg Ala Phe Pro Thr Ile Leu Phe Val Lys Ala Gly Thr Arg Thr
            435                 440                 445

Pro Ile Pro Tyr Asp Gly Lys Arg Thr Val Glu Ala Phe Lys Glu Phe
            450                 455                 460

Ile Ser Glu His Ser Ser Phe Pro Gln Glu Lys Glu Ser Arg Asp Glu
465                 470                 475                 480

Leu
```

<210> SEQ ID NO 10
<211> LENGTH: 508
<212> TYPE: PRT
<213> ORGANISM: Homo sapiens

<400> SEQUENCE: 10

```
Met Leu Arg Arg Ala Leu Leu Cys Leu Ala Val Ala Ala Leu Val Arg
1               5                   10                  15

Ala Asp Ala Pro Glu Glu Glu Asp His Val Leu Val Leu Arg Lys Ser
            20                  25                  30

Asn Phe Ala Glu Ala Leu Ala Ala His Lys Tyr Leu Leu Val Glu Phe
            35                  40                  45

Tyr Ala Pro Trp Cys Gly His Cys Lys Ala Leu Ala Pro Glu Tyr Ala
    50                  55                  60

Lys Ala Ala Gly Lys Leu Lys Ala Glu Gly Ser Glu Ile Arg Leu Ala
65              70                  75                  80

Lys Val Asp Ala Thr Glu Glu Ser Asp Leu Ala Gln Gln Tyr Gly Val
            85                  90                  95

Arg Gly Tyr Pro Thr Ile Lys Phe Phe Arg Asn Gly Asp Thr Ala Ser
            100                 105                 110

Pro Lys Glu Tyr Thr Ala Gly Arg Glu Ala Asp Asp Ile Val Asn Trp
            115                 120                 125

Leu Lys Lys Arg Thr Gly Pro Ala Ala Thr Thr Leu Pro Asp Gly Ala
130             135                 140

Ala Ala Glu Ser Leu Val Glu Ser Ser Glu Val Ala Val Ile Gly Phe
145                 150                 155                 160

Phe Lys Asp Val Glu Ser Asp Ser Ala Lys Gln Phe Leu Gln Ala Ala
            165                 170                 175

Glu Ala Ile Asp Asp Ile Pro Phe Gly Ile Thr Ser Asn Ser Asp Val
            180                 185                 190
```

-continued

```
Phe Ser Lys Tyr Gln Leu Asp Lys Asp Gly Val Val Leu Phe Lys Lys
        195                 200                 205

Phe Asp Glu Gly Arg Asn Asn Phe Glu Gly Glu Val Thr Lys Glu Asn
        210                 215                 220

Leu Leu Asp Phe Ile Lys His Asn Gln Leu Pro Leu Val Ile Glu Phe
225             230                 235                 240

Thr Glu Gln Thr Ala Pro Lys Ile Phe Gly Gly Glu Ile Lys Thr His
                245                 250                 255

Ile Leu Leu Phe Leu Pro Lys Ser Val Ser Asp Tyr Asp Gly Lys Leu
                260                 265                 270

Ser Asn Phe Lys Thr Ala Ala Glu Ser Phe Lys Gly Lys Ile Leu Phe
        275                 280                 285

Ile Phe Ile Asp Ser Asp His Thr Asp Asn Gln Arg Ile Leu Glu Phe
        290                 295                 300

Phe Gly Leu Lys Lys Glu Glu Cys Pro Ala Val Arg Leu Ile Thr Leu
305             310                 315                 320

Glu Glu Glu Met Thr Lys Tyr Lys Pro Glu Ser Glu Leu Thr Ala
                325                 330                 335

Glu Arg Ile Thr Glu Phe Cys His Arg Phe Leu Glu Gly Lys Ile Lys
                340                 345                 350

Pro His Leu Met Ser Gln Glu Leu Pro Glu Asp Trp Asp Lys Gln Pro
        355                 360                 365

Val Lys Val Leu Val Gly Lys Asn Phe Glu Asp Val Ala Phe Asp Glu
        370                 375                 380

Lys Lys Asn Val Phe Val Glu Phe Tyr Ala Pro Trp Cys Gly His Cys
385             390                 395                 400

Lys Gln Leu Ala Pro Ile Trp Asp Lys Leu Gly Glu Thr Tyr Lys Asp
                405                 410                 415

His Glu Asn Ile Val Ile Ala Lys Met Asp Ser Thr Ala Asn Glu Val
                420                 425                 430

Glu Ala Val Lys Val His Ser Phe Pro Thr Leu Lys Phe Phe Pro Ala
        435                 440                 445

Ser Ala Asp Arg Thr Val Ile Asp Tyr Asn Gly Glu Arg Thr Leu Asp
        450                 455                 460

Gly Phe Lys Lys Phe Leu Glu Ser Gly Gly Gln Asp Gly Ala Gly Asp
465                 470                 475                 480

Asp Asp Asp Leu Glu Asp Leu Glu Glu Ala Glu Glu Pro Asp Met Glu
                485                 490                 495

Glu Asp Asp Asp Gln Lys Ala Val Lys Asp Glu Leu
                500                 505
```